(12) United States Patent
Delgass et al.

(10) Patent No.: US 9,783,474 B2
(45) Date of Patent: Oct. 10, 2017

(54) CATALYTIC BIOMASS CONVERSION METHODS, CATALYSTS, AND METHODS OF MAKING THE SAME

(71) Applicant: PURDUE RESEARCH FOUNDATION, West Lafayette, IN (US)

(72) Inventors: William Nicholas Delgass, West Lafayette, IN (US); Rakesh Agrawal, West Lafayette, IN (US); Fabio Henrique Ribeiro, West Lafayette, IN (US); Basudeb Saha, West Lafayette, IN (US); Sara Lynn Yohe, West Lafayette, IN (US); Mahdi M Abu-Omar, West Lafayette, IN (US); Trenton Parsell, Lafayette, IN (US); Paul James Dietrich, Naperville, IL (US); Ian Michael Klein, Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 0 days.

(21) Appl. No.: 15/032,218

(22) PCT Filed: Oct. 27, 2014

(86) PCT No.: PCT/US2014/062471
§ 371 (c)(1),
(2) Date: Apr. 26, 2016

(87) PCT Pub. No.: WO2015/061802
PCT Pub. Date: Apr. 30, 2015

(65) Prior Publication Data
US 2016/0289150 A1 Oct. 6, 2016

Related U.S. Application Data

(60) Provisional application No. 61/896,110, filed on Oct. 27, 2013.

(51) Int. Cl.
*C07C 41/18* (2006.01)
*C10L 1/02* (2006.01)
(Continued)

(52) U.S. Cl.
CPC ............... *C07C 41/18* (2013.01); *B01J 21/18* (2013.01); *B01J 21/185* (2013.01); *B01J 23/60* (2013.01);
(Continued)

(58) Field of Classification Search
None
See application file for complete search history.

(56) References Cited

U.S. PATENT DOCUMENTS

2010/0298125 A1* 11/2010 Kim ................... B01J 21/185
502/185
2012/0167876 A1* 7/2012 Qiao ........................ C13K 1/02
127/37

(Continued)

OTHER PUBLICATIONS

Parsell et al. ("Cleavage and hydrodoxygenation (HDO) of C-O bonds relevant to lignin conversion using Pd/Zn synergistic catalysis", Chemical Science, vol. 4, No. 2, Nov. 2012, pp. 806-813).*
(Continued)

*Primary Examiner* — Rosalynd Keys
(74) *Attorney, Agent, or Firm* — Purdue Research Foundation

(57) ABSTRACT

Described herein are processes for one-step delignification and hydrodeoxygenation of lignin fraction a biomass feedstock. The lignin feedstock is derived from by-products of paper production and biorefineries. Additionally described is
(Continued)

a process for converting biomass-derived oxygenates to lower oxygen-content compounds and/or hydrocarbons in the liquid or vapor phase in a reactor system containing hydrogen and a catalyst comprised of a hydrogenation function and/or an oxophilic function and/or an acid function. Finally, also described herein is a process for converting biomass-derived oxygenates to lower oxygen-content compounds and/or hydrocarbons in the liquid or vapor phase in a reactor system containing hydrogen and a catalyst comprised of a hydrogenation function and/or an oxophilic function and/or an acid function.

15 Claims, 19 Drawing Sheets

(51) Int. Cl.
| | |
|---|---|
| *B01J 23/60* | (2006.01) |
| *D21C 9/00* | (2006.01) |
| *C08H 7/00* | (2011.01) |
| *C08H 8/00* | (2010.01) |
| *D21C 3/22* | (2006.01) |
| *C07C 41/01* | (2006.01) |
| *C07G 1/00* | (2011.01) |
| *C07D 307/48* | (2006.01) |
| *C07D 307/50* | (2006.01) |
| *B01J 21/18* | (2006.01) |
| *B01J 23/652* | (2006.01) |
| *C07C 1/22* | (2006.01) |
| *C07D 307/46* | (2006.01) |
| *C10L 1/04* | (2006.01) |

(52) U.S. Cl.
CPC ............ *B01J 23/6525* (2013.01); *C07C 1/22* (2013.01); *C07C 41/01* (2013.01); *C07D 307/46* (2013.01); *C07D 307/48* (2013.01); *C07D 307/50* (2013.01); *C07G 1/00* (2013.01); *C08H 6/00* (2013.01); *C08H 8/00* (2013.01); *C10L 1/02* (2013.01); *C10L 1/04* (2013.01); *D21C 3/222* (2013.01); *D21C 9/00* (2013.01); *C07C 2521/18* (2013.01); *C07C 2523/60* (2013.01); *C07C 2523/64* (2013.01); *C10L 2200/0469* (2013.01)

(56) References Cited

U.S. PATENT DOCUMENTS

| | | | | |
|---|---|---|---|---|
| 2013/0232853 | A1* | 9/2013 | Peterson | C07G 1/00 44/307 |
| 2015/0337214 | A1* | 11/2015 | Murray | C10G 3/45 585/357 |

OTHER PUBLICATIONS

Dietrich et al. ("Aqueous Phase Glycerol Reforming by Pt/Mo Bimetallic Nano-Particle Catalyst: Product Selectivity and Structural Characterization", Topic in Catalysis, Feb. 2012, vol. 55, Nos. 1-2, pp. 53-69).*

* cited by examiner

CATALYTIC BIOMASS CONVERSION METHODS, CATALYSTS, AND METHODS OF MAKING THE SAME

CROSS-REFERENCE TO RELATED APPLICATIONS

The present non-provisional patent application is a U.S. §371 national stage entry of International Patent Application Serial No. PCT/US2014/062471 filed Oct. 27, 2014, which is related to and claims the priority benefit of U.S. Provisional Patent Application Ser. No. 61/896,110, filed Oct. 27, 2013, the contents of which is hereby incorporated by reference in its entirety into the present disclosure.

GOVERNMENT SUPPORT

This invention was made with government support under DE-SC0000997 awarded by the U.S. Department of Energy; DE-FG36-08DO18087 awarded by the U.S. Department of Energy; DGE-1333468 awarded by the National Science Foundation; and DGE-0938033 awarded by the National Science Foundation. The government has certain rights in the invention.

TECHNICAL FIELD

The present disclosure relates generally to renewable fuels, and more particularly to catalytic conversion of biomass to commercially relevant commodity chemicals and biofuels.

BACKGROUND

Irreversible consumption of carbon sources result in depletion of fossil fuels reserves and global warming by carbon dioxide emission. This issue has prompted researchers to explore non-conventional resources, including non-food biomass, for large scale production of chemicals and fuels, particularly after the U.S. Department of Energy published a list of "ten bio-based chemicals" of top priority. Among these top priority chemicals, 5-hydroxymethylfurfural (HMF) and furfural (Ff) have received significant attention as platform chemicals for producing a broad range of chemicals and liquid transportation fuels. Despite the versatile applications of furfurals, rapid progress in developing efficient catalytic processes for conversion of carbohydrates and biomass has been witnessed over the past few years, but sustainable and economically viable routes for their production in scalable quantities has been slow to develop further.

Production of liquid fuels and chemicals from lignocellulosic plant matter (hereinafter referred to as biomass) is another integral solution to the energy grand challenge because it offers an alternative to petroleum based feedstocks. Further, "cellulosic" ethanol made from corn stalks and other agricultural feedstocks are heading towards commercialization. "Cellulosic" ethanol and other conversion methods do not make full use of the carbohydrate components of biomass (ca. 60% by weight), due to carbon loss to $CO_2$ during fermentation of free sugars. It is noteworthy to mention as well that some modern processes also do not utilize the hemicellulose component to make ethanol due to limitations of the yeast. Regarding cellulosic ethanol and other conversion methods, they either neglect or underutilize the lignin component, a significant portion of wood biomass (15-25 wt %). Currently, most lignin is burned to produce electricity in the pulping industry and in biorefineries. As a complex biopolymer, lignin lends structural integrity to plants. Since it is composed of ether linked phenylpropanolic units, lignin contains less oxygen per carbon atom than carbohydrates (cellulose and hemicellulose) and hence, comprises ca. 40% of the energy available in biomass prior to conversion or upgrading.

Referring to FIG. 1, lignin is made by radical polymerization of three monomers (G, S, and H) to give various linkage types. The most ubiquitous linkage is the β-O-4. G, S, and H incorporation into the lignin biopolymers varies depending on the plant species and the availability of different monomers can be manipulated genetically. Moreover, this availability ultimately affects the overall lignin polymer composition in the plant. Furthermore, lignin is the only large volume renewable feedstock composed of aromatics, making it an attractive source for high value aromatic compounds, which comprise four of the top twenty chemicals in the U.S. It is noteworthy that this has been considered an attractive fuel due to the high octane.

Despite extensive research, conversion of lignin to discrete aromatic compounds remains a significant challenge. The only notable commercial process is the production of vanillin from ligno-sulfonates at a mere maximum yield of 7.5% by mass. There have been more notable developments in producing aromatics from nonaromatic biomass sources, such as bio-based styrene from butadiene produced from bio-ethanol or bio-butanol. Even though new catalysts have been reported for the cleavage of ether C—O bonds and hydrodeoxygenation (HDO) of lignin model compounds, only limited successes have been reported with lignin or biomass feedstocks. Heterogeneous Ni catalysts have been used recently with lignosulfonates to give a mixture of phenolic compounds and dimeric lignin fragments with removal of the sulfur as $H_2S$. Ford et al. have reported a catalytic method in supercritical methanol at 300-320° C. and 160-220 bar of $H_2$ that convert the lignified components of biomass to hydrogenated cyclic alcohols. Current methods for extraction of lignin into what is commonly known as "organosolv" lignin produce complex mixtures containing hundreds of phenolic products, none of which occur in large yields. However, universal conversion of these mixtures to valuable aromatic chemicals in a single stream product is difficult.

Aside from seeking conversion processes which produce a narrower stream of products, another approach that could be proposed is related to control of the lignin production pathway in plants. Through regulation of genes along this pathway, the base composition of lignin can be made more homogenous or even changed to contain non-native types of phenolic moieties. These techniques of biologically tailoring the biomass have great potential to create lignin that is not only easier to extract from plants in a selective manner but could also contain products that are unattainable from wild type plants.

Another widely studied approach of biomass conversion is gasification, where biomass is thermally decomposed in the presence of steam and oxygen to smaller compounds, such as carbon monoxide (CO) and hydrogen ($H_2$), at temperatures near 800° C.-1000° C. The $H_2$ and CO produced are subsequently recombined at lower temperatures of 250° C.-350° C. over a catalyst. This method, however, does not exploit the existing structure of the starting biomass and suffers from low overall process energy efficiency (which is defined as the ratio of energy in the products to the energy of the starting biomass and any other energy input).

Yet another approach for converting biomass to high energy density fuels and fine chemicals is liquid-phase upgrading processes. However, many of these processes do not convert the lignin fraction of biomass, thereby suppressing carbon recovery. Additional challenges to liquid-phase upgrading include finding a solvent that does not decompose at process pressures and temperatures.

Another approach for converting biomass to biofuels and other chemical commodities is based on biomass fast-pyrolysis, where biomass is thermally decomposed at 400° C.-600° C. in the presence of an inert gas to intermediate carbon chain length compounds (between 6-12 carbon atoms), which are condensed and collected as a liquid, referred to as bio-oil. This bio-oil is subsequently reacted in the liquid or vapor phase in the presence of $H_2$ and catalytically active materials at 400° C.-600° C. to be converted to hydrocarbons. Due to the reactive nature of the oxygen containing compounds formed during fast-pyrolysis, the bio-oil tends to be unstable, acidic, and is of relatively low energy density. Therefore, re-heating of the condensed bio-oil can lead to condensation reactions that degrade the product and inhibit effective upgrading to deoxygenated hydrocarbon products.

Therefore, there is an unmet need for an energetically efficient, high yield process and catalyst that converts biomass to biofuels and other high value commodity chemicals.

SUMMARY

A process for one-step delignification and hydrodeoxygenation of lignin fraction of a biomass feedstock is disclosed herein. The process comprises contacting the biomass with a selective hydrodeoxygenation catalyst at predetermined processing conditions to form high value organic molecules selected from the group consisting of dihydroeugenol (2-methoxy-4-propylphenol, 2,6-dimethoxy-4-propylphenol, or a mixture of both dihydroeugenol and 2,6-dimethoxy-4-propylphenols.

Also described herein is a process for converting biomass-derived oxygenates to lower oxygen-content compounds and/or hydrocarbons in the liquid or vapor phase in a reactor system containing hydrogen and a catalyst comprised of a hydrogenation function and/or an oxophilic function and/or an acid function.

Additionally described herein is a process for producing 5-hydroxymethylfurfural and furfural from carbohydrate fraction of a biomass feedstock, comprising exposing the biomass to a biorenewable solid acid catalyst containing both Lewis and Brønsted acid sites.

DETAILED DESCRIPTION OF THE EXEMPLARY EMBODIMENTS

Figure 1:
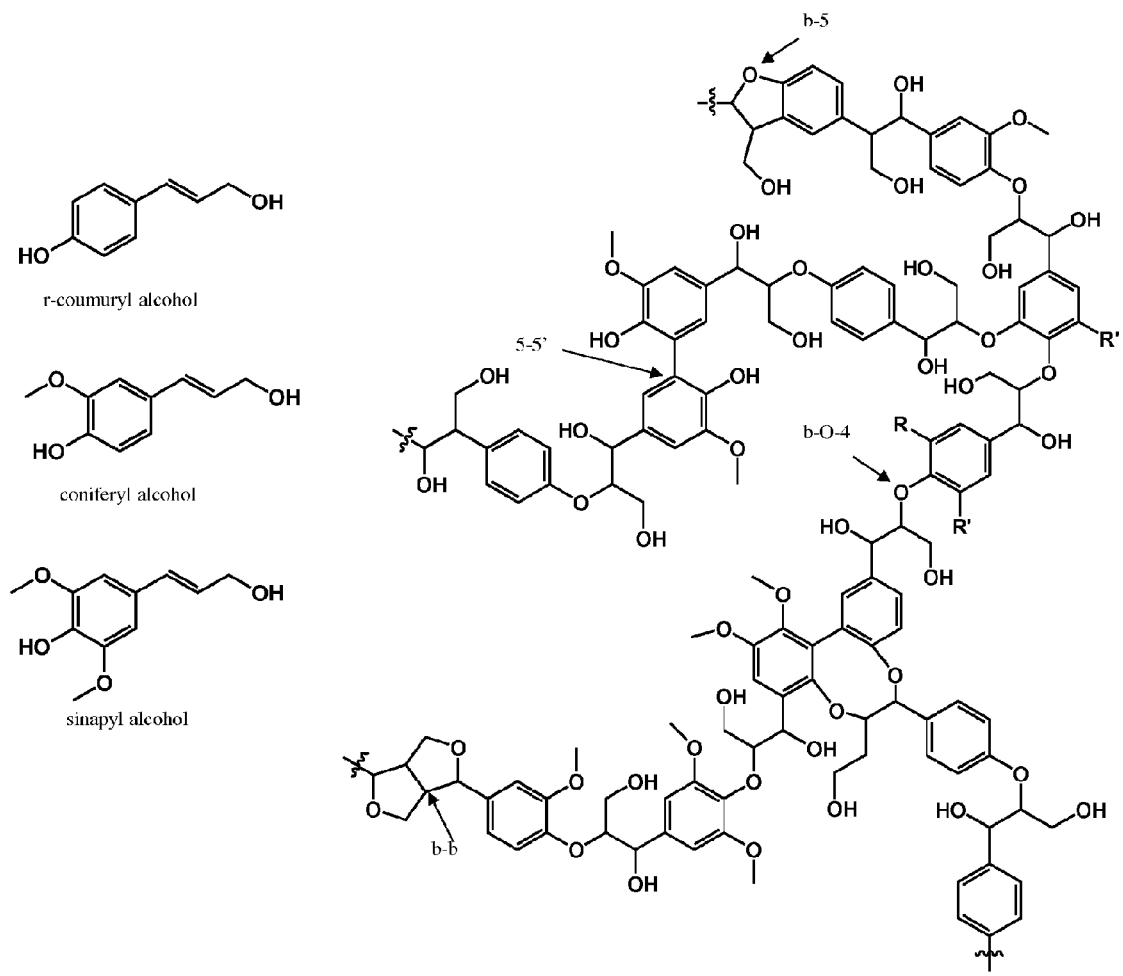
FIG. 1 depicts a representative lignin structure originating from p-coumuryl (H), coniferyl (G), and sinapyl alcohol (S).

For the purposes of promoting an understanding of the principles of the disclosure, reference will now be made to the embodiments illustrated in the drawings and specific language will be used to describe the same. It will nevertheless be understood that no limitation of the scope of the disclosure is thereby intended, such alterations and further modifications in the illustrated device, and such further applications of the principles of the disclosure as illustrated therein being contemplated as would normally occur to one skilled in the art to which the disclosure relates. At least one embodiment of the present disclosure will be described and shown, and this application may show and/or describe other embodiments of the present disclosure. It is understood that any reference to "the disclosure" is a reference to an embodiment of a family of disclosures, with no single embodiment including an apparatus, process, or composition that should be included in all embodiments, unless otherwise stated. Further, although there may be discussion with regards to "advantages" provided by some embodiments of the present disclosure, it is understood that yet other embodiments may not include those same advantages, or may include yet different advantages. Any advantages described herein are not to be construed as limiting to any of the claims.

Native biomass represents a sustainable carbon source to synthesize fuels and chemicals to offset conventional fossil fuel sources. However, although biomass contains carbon atoms linked with each other, it also contains oxygen present as various functional groups (ketones, aldehydes, hydroxyls, etc.), amounting to 40-50 wt % of the biomass. Due to the oxygen content, biomass has a lower energy density compared to fossil fuels. In addition, these oxygen functional groups lead to the reactive and acidic nature of the biomass-derived compounds.

Figure 2:
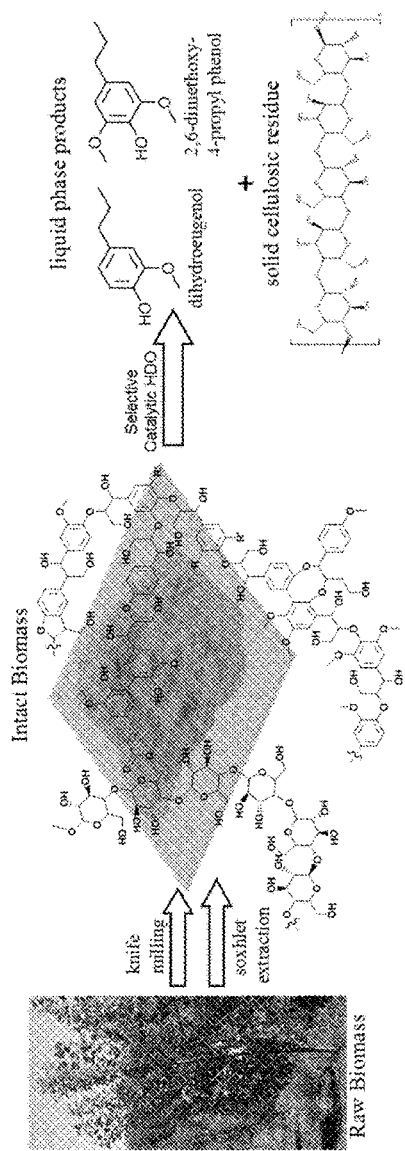
FIG. 2 depicts the scheme of selective depolymerization and a partial view of hydrodeoxygenation (HDO) of lignin from wood biomass in one step.

One embodiment presented herein entails a selective conversion process compatible with intact wood biomass that has undergone minimal pretreatment, namely drying and knife milling. Referring to FIG. 2, the disclosed catalytic process employs a bifunctional catalyst based on zinc and nanoparticulate Pd/C, and produces a single product stream, methoxypropylphenol, in high yields leaving the cellulosic portion of the biomass as a solid residue available for further utilization. The mass balance has been fully closed to 90% of the starting biomass by quantifying the sugar content in the cellulosic residue following lignin conversion. The availability of the cellulosic residue for further conversion was realized by subjecting it to fast pyrolysis, giving nearly identical results to that obtained with pure cellulose. Furthermore, herein it is demonstrated that the resulting products can be tailored through genetic manipulation of the plants lignin production processes to change the product distribution.

The main highlights of this embodiment are (1) the use of intact hardwoods (though the disclosed process would also work on other biomass such as pine, birch, and eucalyptus) that are bioenergy relevant feedstock such as poplar, (2) the process is selective giving a single product stream, (3) one step reaction gives high conversion of lignin with separation of the products into the liquid stream, and (4) the leftover solid residue accounts for the cellulosic content and remains amenable for further conversion. This last point underscores the power of the disclosed catalytic process as it provides a new way of thinking regarding lignin. Instead of the conventional biorefinery approach to address lignin utilization last, here the feasibility of getting the value from lignin upfront as it is being removed without losing the cellulose is illustrated.

Figure 3:
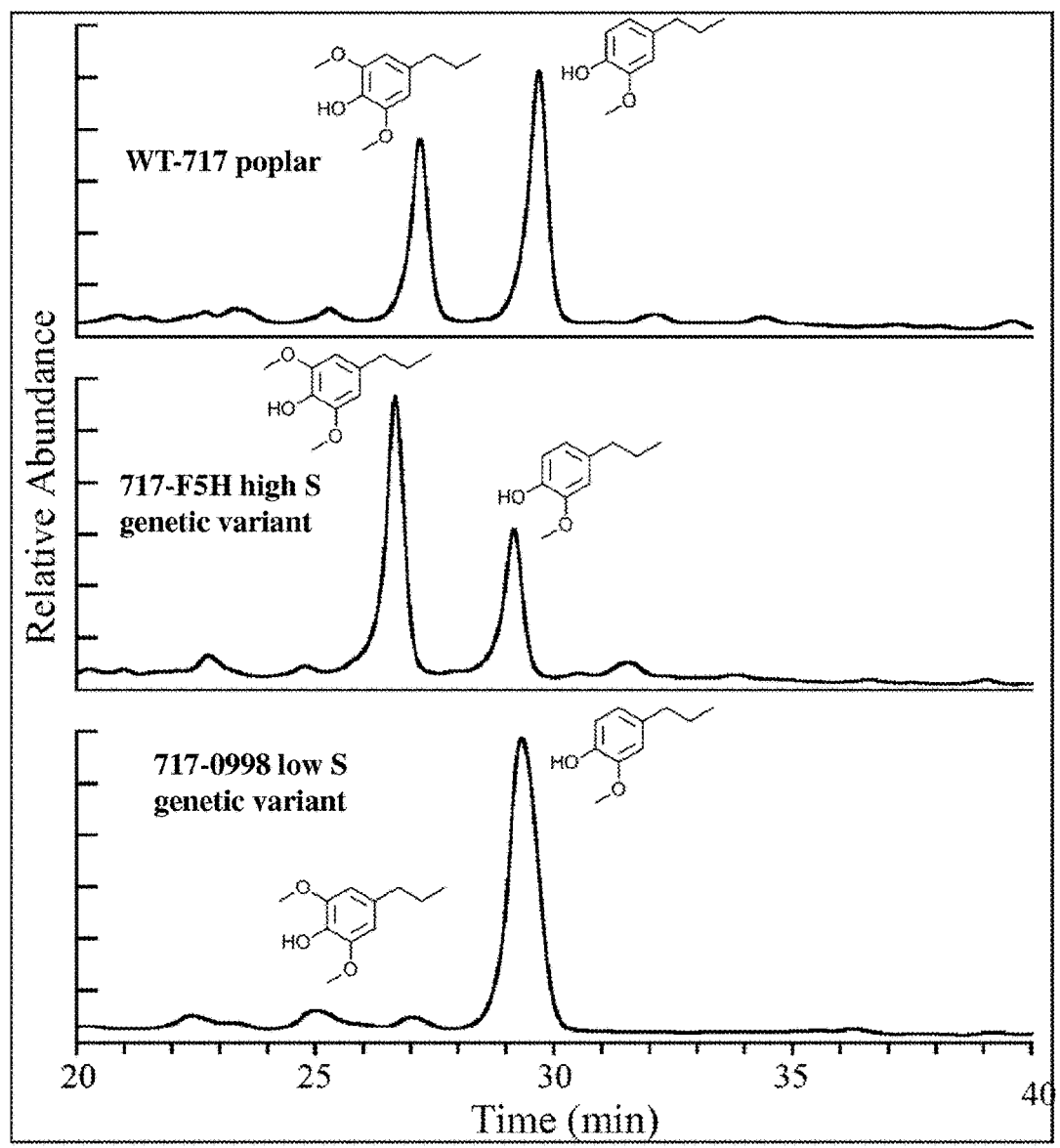
FIG. 3 depicts the HPLC-MS of lignin products from WT-717 poplar, 717-F5H high S genetic variant, and 717-0998 low S genetic variant.
Figure 4A:
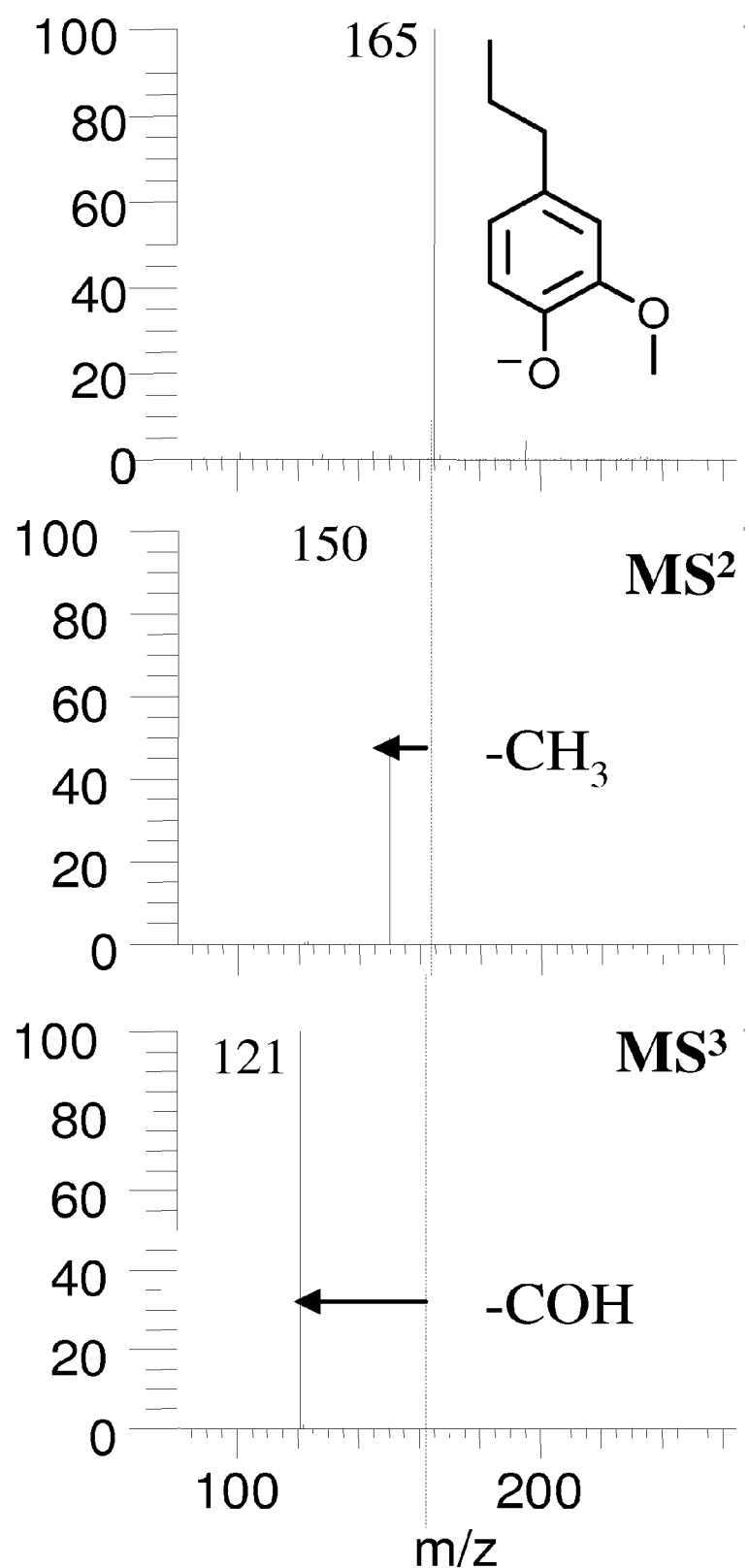
FIG. 4a depicts the CAD MS/MS of dihydroeugenol.
Figure 4B:
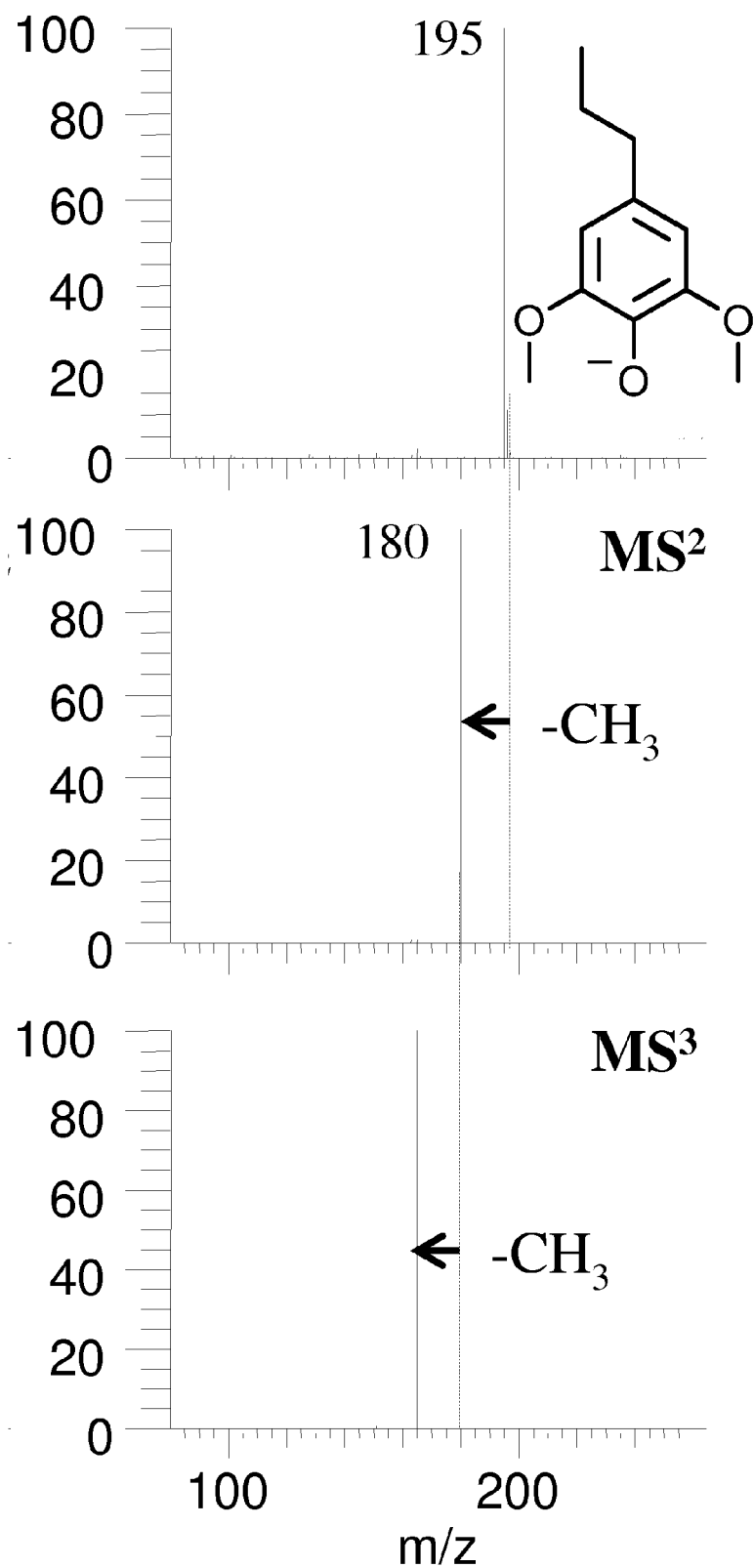
FIG. 4b depicts the CAD MS/MS of 2,6-dimethoxy-4-propyl phenol.

Referring to Table 1 below (entries 1, 4 and 5) and FIGS. 3, 4a, and 4b, treatment of three different species of wild type (WT) poplar wood with the Zn/Pd/C catalyst in methanol (MeOH) at 225° C. and 34 bar of $H_2$ resulted in 40-54% of the available biomass lignin being converted to 2-methoxy-4-propylphenol (dihydroeugenol) (FIG. 4a, which is a CAD MS/MS of dihydroeugenol) and 2,6-dimethoxy-4-propylphenol (FIG. 4b, which is a CAD MS/MS of 2,6-dimethoxy-4-propyl phenol). Prior to catalysis, the employed biomass was dried, knife milled, and soxhlet extracted in ethanol and water. The last step is a conventional pretreatment to remove waxes and small molecules and results in minimal mass loss from the biomass (5-10 wt %). However, in the case of poplar the soxhlet extraction was not a necessary step. Similar results were obtained without it. The described preparation/pretreatment of biomass is minimal and all the steps are scalable, an important prerequisite of any process for large scale application. The two products reflect G and S lignin components present in WT poplar. The catalyst is composed of Lewis acidic zinc(II) sites and metallic Pd(0) nanoparticles (3-4 nm). Through X-ray absorption spectroscopy, the development and characterization of the catalyst disclosed herein has been shown. Its bifunctional utility in cleaving ether C—O bonds and hydrodeoxygenation (HDO) of synthetic dimeric and oligomeric lignin surrogates has also been demonstrated. Zinc adsorbs on C in the 2+ oxidation state; under high temperature it is mobile into the liquid phase and hypothesized to facilitates C—O ether cleavage lignin linkages. It also plays a synergistic effect with Pd on the surface in making the Pd—H catalyst selective for HDO of C—O bonds leaving the aromatic functionality unscathed. This last feature is important as it avoids wasting $H_2$ unnecessarily. Upon cooling the batch reaction, Zn is re-adsorbed on the C surface avoiding the need to add Zn for each subsequent reaction.

TABLE 1

Conversion of lignin using intact wood biomass over Zn/Pd/C catalyst.

| Biomass Type | % G Lignan[a] | % S Lignin[a] | % Lignin Content[b] | Selectivity (4-propyl guaiacol) | Selectivity (4-propyl syringol) | Yield (wt %)[c] |
|---|---|---|---|---|---|---|
| Poplar WT-717 | 44 | 51 | 19 | 31 | 69 | 40 |
| Poplar 717-0998 (Low S Poplar) | 89 | 7 | 19 | 90 | 10 | 27 |
| Poplar 717-F5H (High S Poplar) | 20 | 73 | 20 | 17 | 83 | 36 |
| Poplar WT-NM-6 | 40 | 55 | 18 | 28 | 72 | 44 |
| Poplar WT-LORRE | 49 | 47 | 19 | 45 | 55 | 54 |
| WT-White Birch | 44 | 49 | 16 | 31 | 69 | 52 |
| WT-Eucalyptus | 34 | 65 | 24 | 30 | 70 | 49 |
| WT-Lodgepole Pine | 100 | 0 | 31 | 100 | NA | 19 |

Both Zn and Pd are required for catalysis. Control reactions with poplar using Zn alone give minimal conversion (no products) to multiple oxygenated products. Reactions of poplar wood with Pd/C alone give small yields (~8%) of methoxypropylphenol products. Hydrogen is also needed as the MeOH solvent does not serve as a reductant under these reaction conditions for lignin HDO.

Since the lignin content (determined by Acetyl Bromide-soluble Lignin analysis) of the WT poplar samples used herein is approximately 19% (see Table 1 above, entries 1-3), a single product stream was able to be achieved for >10 wt % of the whole intact biomass. Dihydroeugenol is a high value chemical that is widely used in the flavoring and fragrance industries with annual production of 15 million Kg at a global market value of $450 million in 2009. It is produced via multiple steps from petroleum feedstock (cumene). The remaining balance of the starting biomass remains as a solid residue while the methoxypropylphenol products are present in the liquid phase. The solvent, methanol, is volatile and easily recycled yielding an easy separation of the products from lignin. The cellulosic residue was digested by acid hydrolysis. The resulting sugars were analyzed allowing for full mass balance closure to better than 90% of the starting biomass weight. To facilitate separation and recycling of the Zn/Pd/C catalyst, the reaction was carried out employing a micorporous cage (325 mesh) containing the catalyst. Such a cage allows the solvent and solute to access the catalyst and leaves behind a cellulosic biomass residue that is catalyst free. The lignin degradation to smaller fragments is initiated by the Zn(II) which is mobile in and out of the catalyst cage.

In addition to WT-717 poplar, two genetic variants, high and low S lignin, were employed (Table 1, entries 4 and 5). The results from these experiments illustrate the power of combining genetic variants with selective catalytic transformation. Referring to FIG. 3: the low S variant (717-0998) yielded 2-methoxy-4-propylphenol (dihydroeugenol) almost exclusively with 9:1 selectivity over 2,6-dimethoxy-4-propylphenol; the high S variant (717-F5H) gave the opposite selectivity with 2,6-dimethoxy-4-propylphenol being the major product in 6:1 selectivity. While unmodified WT-717 has a ~1:2 selectivity of dihydroeugenol to 2,6-dimethoxy-4-propylphenol. These results illustrate how one can select for a single product using the power of genetic modification.

Referring to Table 1 (entries 6, 7, and 8), other woods, pine, eucalyptus, and white birch, can also be transformed by the catalyst disclosed herein. Pine is interesting for two main reasons. First, it contains exclusively G lignin and has a very high lignin content (30 wt %). In addition, pine gave exclusively 2-methoxy-4-propylphenol (dihydroeugenol) but with lower yield compared to the hardwoods. The combination of high lignin content (24% by weight) and high yield (49%) from the eucalyptus sample produced the greatest overall yield of products from a mass standpoint (ca. 12% of the total biomass converted to the two phenolic products). While the lignin content of white birch is only 16 wt %, it gave an impressive yield (52%) composed of the expected mixture of S and G lignin (Table 1, entry 5).

Recently, a report by Xu et al. appeared in literature claiming high yields (ca. 50%) of methoxypropylphenol products from saw dust birch biomass using exclusively heterogeneous Ni/C without the need for hydrogen. Experiments were accordingly conducted under the reported conditions with white birch biomass using Ni/C as a catalyst in MeOH. In the absence of hydrogen, no conversion was observed. After washing and drying the Ni/C catalyst, no conversion was observed of birch under hydrogen (200° C., 500 psi $H_2$ for 12 h). When the prepared Ni/C was used without washing and under hydrogen, minimal conversion was observed (approximately 2%) to methoxypropylphenol products. The results disclosed herein bring to light the limitation of the claimed report to the particular saw dust biomass employed in the literature report (Xu, et al.).

Figure 5:
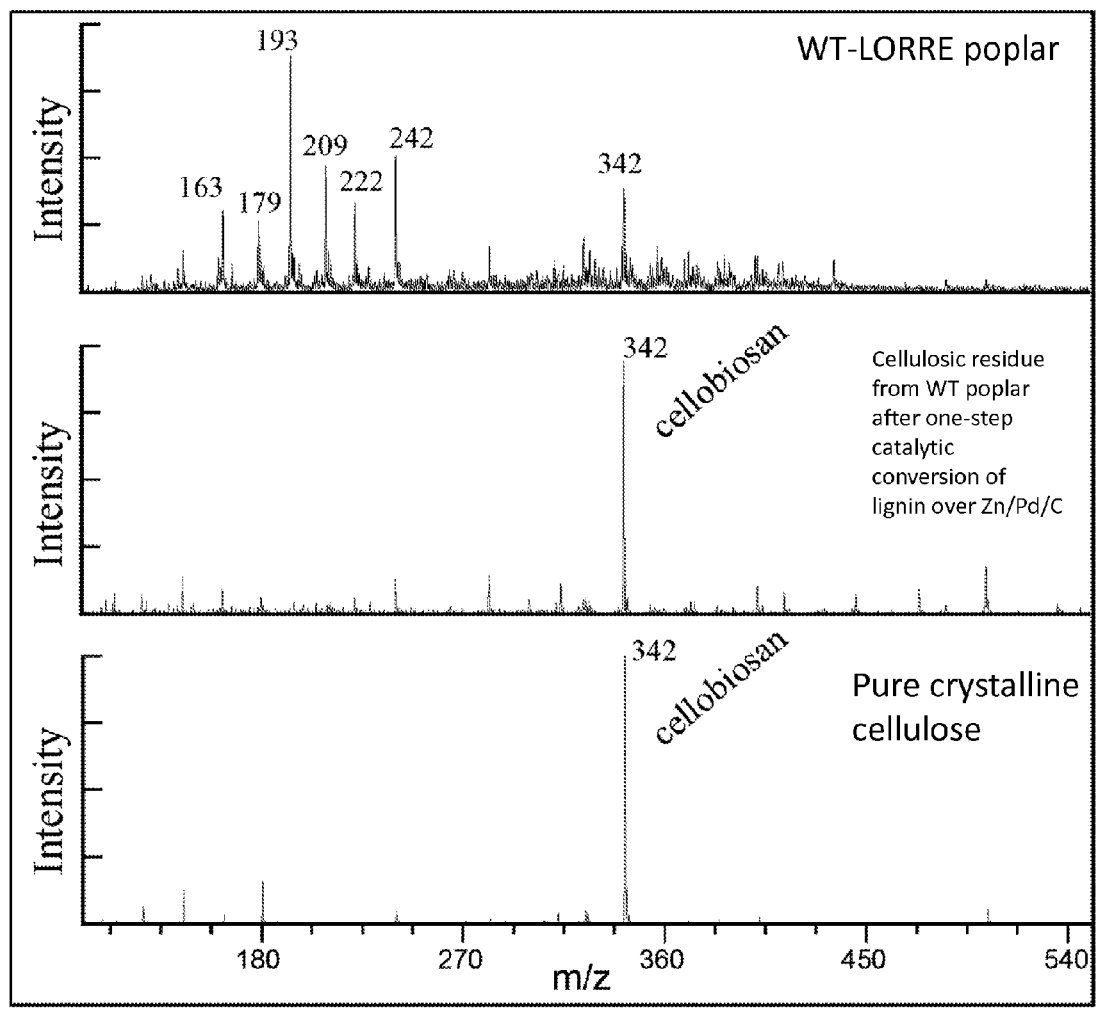
FIG. 5 shows the results of pyrolysis reactions of WT-Lorre poplar, cellulosic residue from WT poplar after the disclosed one-step conversion of lignin over Zn/Pd/C, and pure crystalline cellulose.

The availability of the leftover cellulosic residue for further conversion to liquid fuels and/or high value chemicals was demonstrated by subjecting the sample to fast-pyrolysis. FIG. 5 illustrates the results of the pyrolysis reactions along with comparisons to pure cellulose and whole wood biomass. The cellulosic residue after the catalytic HDO conversion of lignin disclosed herein behaved similarly to the pyrolysis of pure cellulose yielding a similar product distribution, the main product of which is cellobiosan, this is in sharp contrast to the highly complex mixture obtained when starting with wood biomass.

Figure 6:
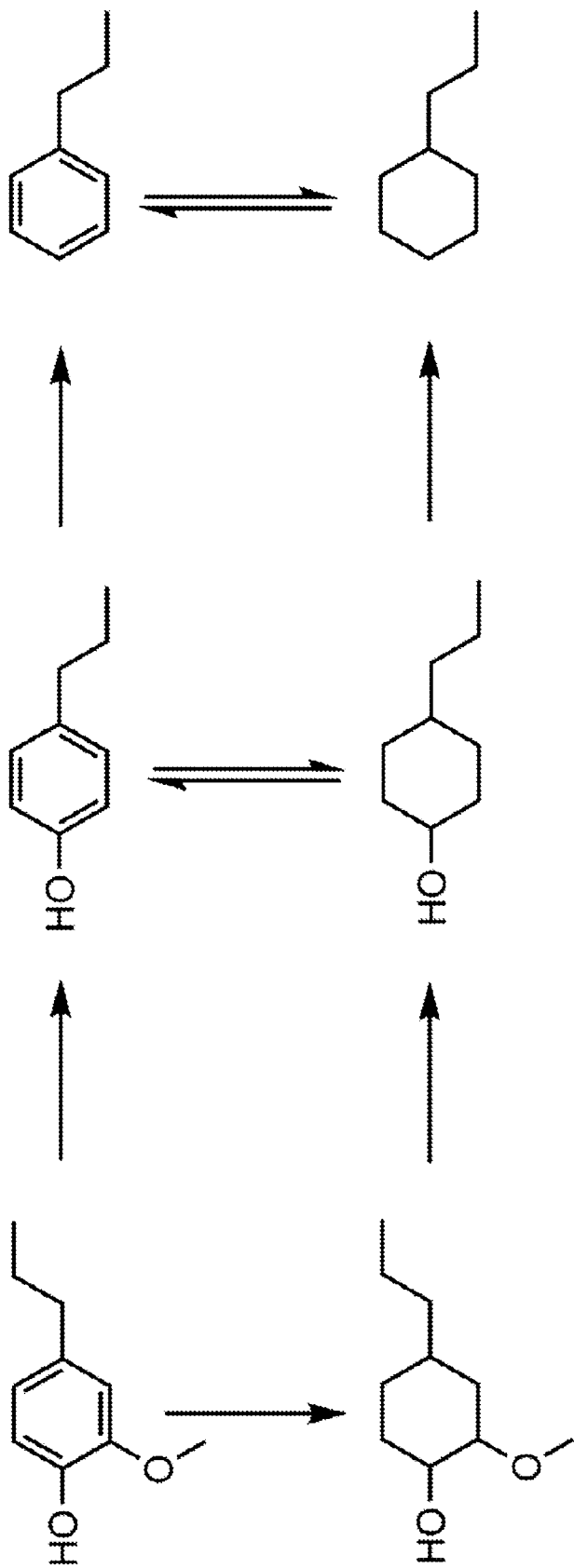
FIG. 6 depicts a reaction scheme for the vapor-phase hydrogenation/hydrodeoxygenation reaction pathway of dihydroeugenol (2-methoxy-4-propylphenol) over a 5% PtMo(1:1)/MWCNT (Multiwalled Carbon Nanotube) catalyst at 300° C. and 350 psi hydrogen to form the hydrocarbons propylcyclohexane and propylbenzene as final products in approximately 98% combined yield.

In addition to the high value of the methoxypropylphenol products, they can also be converted to the high octane liquid fuel propylbenzene. FIG. 6 depicts the vapor-phase hydrogenation/hydrodeoxygenation reaction pathway of dihydroeugenol (2-methoxy-4-propylphenol) over a 5% PtMo(1:1)/MWCNT (Multiwalled Carbon Nanotube) catalyst (discussed herein below) at 300° C. and 350 psi hydrogen to form the hydrocarbons propylcyclohexane and propylbenzene as final products in approximately 98% combined yield. When either 2-methoxy-4-propylphenol (dihydroeugenol) or 2,6-dimethoxy-4-propylphenol is subjected to $H_2$ over a PtMo bimetallic catalyst in the vapor-phase at 300° C. and 350 psi $H_2$, propylcyclohexane and propylbenzene are obtained in quantitative yield (>97.8% and 0.2%, respectively). The propylcyclohexane can be aromatized via a dehydrogenation reaction that is currently practiced in the petrochemical industry to give additional propylbenzene and return 3 equivalents of the hydrogen used in the hydrogenation of dihydroeugenol over the PtMo catalyst.

Catalytic hydrodeoxygenation of lignin to discrete phenolic units was therefore achieved with good yields utilizing a process that produces a relatively clean cellulosic residue. This utilization of lignin as an initial step can add both value and efficiency to processes that depend on biomass. There is great potential to boost yields of phenols and change product distributions of this lignin extraction process to achieve even greater efficiency.

Another embodiment described herein involves a novel process involving catalytically upgrading biomass or oxygenated vapors in a high-pressure hydrogen environment to produce liquid transportation fuels from lignocellulosic biomass feedstocks to overcome challenges faced in current biomass conversion technologies. Among the goals of the processes and methods disclosed herein is to produce liquid hydrocarbon fuels from biomass by selectively removing the oxygen functionality without degrading the carbon structural backbone. The developed reactor system that is disclosed in this embodiment is capable of preserving the existing carbon atom backbone present in native biomass, while making carbon hydrogen bonds and predominately converting the oxygen functional groups to $CO_2$, CO, $H_2O$, $CH_4$ and $CH_3OH$. To accomplish this, the biomass or oxygenated compounds derived from biomass (via pyrolysis, fast-pyrolysis, fast-hydropyrolysis, liquefaction, or liquid-phase conversion, fermentation or anaerobic digestion of biomass, hydrothermal upgrading of biomass, byproducts of paper production such as the Kraft or Organosolv process, or gasification) are catalytically upgraded in the vapor-phase (or liquid-phase for lignin derived compounds) into hydrocarbons or other valuable fuel components. The upgrading occurs via catalytic hydrodeoxygenation to increase the energy content and reduce oxygen content to 0% for some compounds. Catalyst development for hydrodeoxygenation in the vapor-phase remains a challenge, due to catalyst instability and low selectivity to fully deoxygenated products. Lignin upgrading is especially difficult, as the phenol group present in most lignin derived compounds is difficult to remove. Hydrodeoxygenation catalysts must be hydrothermally stable and exhibit long term activity and selectivity toward carbon-oxygen bond cleavage while limiting carbon-carbon bond cleavage reactions.

This embodiment pertains to a high pressure, vapor-phase apparatus and catalyst system that meets the above challenges of hydrodeoxygenation of biomass and biomass derived oxygenated vapors. The result is the production of hydrocarbon compounds from oxygen containing compounds present in biomass at conversions of 100% and yields of >98%. The disclosed embodiment is hydrothermally stable, water tolerant, exhibits limited carbon-carbon cleavage with rapid deoxygenation kinetics, and has been demonstrated to be particularly effective for the removal of oxygen from recalcitrant lignin-derived compounds, specifically removal of the phenolic functionality.

The catalysts studied for this embodiment were bimetallic Platinum (Pt) and Molybdenum (Mo) supported on multi-walled carbon nanotubes (MWCNT). Different compositions of the bimetallic PtMo catalyst have been studied along with other choices of metal with hydrogenation functions (such as Pt, Pd, Ni, Ru, Rh, Co, Fe, etc.) and an oxophilic (i.e., exhibiting a tendency to form oxides by abstraction of oxygen) metals and metal oxides (such as Ti, V, Nb, Cr, Mo, W, Re, Fe, Cu and the corresponding oxides) supported on a high surface area inert catalyst support (such as MWCNT, Carbon, $SiO_2$, $Al_2O_3$, etc.) or an acidic support (such as silica-alumina, a zeolite, etc.)

The disclosed catalyst system exhibits high stability, activity, and selectivity. In addition, the disclosed process can be coupled with various upstream processes (including pyrolysis, fast-pyrolysis, fast-hydropyrolysis, liquefaction, liquid-phase conversion, liquid-phase lignin extraction, fermentation or anaerobic digestion, hydrothermal upgrading, byproducts of paper production, or gasification) to convert biomass-derived oxygenates to hydrocarbons. An important feature of the process is the use of a high-pressure hydrogen environment, which is necessary for the following: (1) promoting the deoxygenation pathway to preferentially remove oxygen as $H_2O$ instead of $CO_2$, which improves carbon retention from the biomass feedstock; (2) improving catalyst hydrodeoxygenation rates and oxygen removal selectivity to form hydrocarbons; and (3) promoting catalyst stability.

The PtMo/MWCNT system disclosed herein has been shown to effectively deoxygenate both the individual lignin and cellulose-derived components of lignocellulosic biomass as well as whole biomass (sorghum). This catalytic system can result in 100% deoxygenation of cellulose into mainly C4-C6 hydrocarbon products. Previous work by others has been done to convert cellulose to hydrocarbons, but in the liquid phase and not in the vapor phase at high pressure. Additionally, 100% deoxygenation of sorghum has also been demonstrated using the disclosed catalyst system. The bimetallic catalyst system composed of Pt and Mo supported on MWCNT shows very high stability, activity, and yields of hydrocarbon products from both pyrolysis vapors, cellulose compounds, and lignin extraction products—higher than other catalysts tested or reported in literature for vapor-phase upgrading.

The disclosed process and apparatus can be easily coupled at the outlet of a high-pressure hydropyrolysis reactor to convert the vapor-phase oxygenated pyrolysis products into hydrocarbons. The $H_2$Bioil process (which is the subject of U.S. Pat. App. No. 60/968,194 (2007)) proposes this process. The $H_2$Bioil process is used to produce liquid transportation fuels from lignocellulosic biomass feedstocks, which overcomes the problems associated with current pyrolysis bio-oil upgrading strategies, one being the difficulty in catalytically upgrading condensed pyrolysis bio-oil. The $H_2$Bioil process involves catalytic fast-hydropyrolysis of biomass at high-pressure in the presence of hydrogen (from solar or nuclear sources) followed by a second-stage fixed-bed catalytic hydrodeoxygenation (HDO) reactor (which is the process disclosed herein). The oxygenated hydropyrolysis vapors are catalytically upgraded in a high-pressure hydrogen environment immediately downstream of the pyrolysis reactor into hydrocarbons, reducing the oxygen content of the final product and preventing secondary reactions that lead to an increase in product distribution complexity.

Additionally, the described process could be coupled with a second upstream liquid-phase catalytic process that extracts lignin from biomass and selectively produces two stable products, dihydroeugenol and 2,6-dimethoxy-4-propylphenol. The process disclosed herein, using a high-pressure vapor-phase reactor, or a liquid-phase reactor, with a PtMo/MWCNT or similar catalyst in a hydrogen environment can be used to completely deoxygenate these two lignin extraction products (dihydroeugenol and 2,6-dimethoxy-4-propylphenol), generating the hydrocarbon product propylcyclohexane in >97% yield. Propylcyclohexane can be reacted using common petrochemical refining practices (for example, reforming, aromatization) to form higher octane molecules for use as fuel blendstocks (i.e., propylbenzene).

In yet another embodiment, several heterogeneous Lewis acidic mesoporous materials have been tested as solid catalysts. Watanabe et al. used anatase-$TiO_2$ catalyst for fructose and glucose conversions to HMF reporting 38 and 7.7% yields, respectively. More recently self-assembly mesoporous $TiO_2$ nanospheres via templating pathways and hierarchically porous titanium phosphate (MTiP-1) having different Lewis acidity and surface area have been synthesized and tested for HMF production. Besides titanium based solid acids, the catalytic efficiency of MCM-41, Nafion 117, Zr—P, $SiO_2$—$Al_2O_3$, $WO_x/ZrO_2$, $\gamma$-$Al_2O_3$, HY-Zeolite catalysts have also been explored for xylose to Furfural conversions. Although the Lewis acidic solid catalysts are promising in terms of recyclability and easy separation, they suffer from poor yield and selectivity, particularly in an aqueous medium. It has been reported that exposure of Lewis acidic solid catalysts to a polar solvent such as water can potentially alter the intrinsic nature of the surface due to solvation effects. For instance, hydroxyl ions from water (Lewis base) can react with Lewis acid sites on the surface. Poisoning of the acid sites by water may also occur depending on the surface hydrophilicity/hydrophobicity of the catalyst.

In contrast to poor activity of Lewis acidic heterogeneous catalysts, functionalized carbonaceous materials having Brønsted acidic sulfonic acid group are promising catalysts due to their high acidity and water-tolerance. It is only recently that sulfonated graphene oxide has been demonstrated to be an efficient carbocatalyst enabling an average 61% yield of furfural from xylose at 200° C. Usually sulfonated carbonaceous materials are synthesized by two step processes involving preparation of carbonaceous materials in the first step followed by incorporation of —$SO_3H$ group under harsh oxidation conditions using fuming sulfuric acid. To avoid harsh reaction conditions, Wang et al. developed a one-pot synthesis method for sulfonated carbonaceous material by reacting glucose (Glu) and p-toluenesulfonic acid (TsOH) in a sealed autoclave at 180° C., and reported its efficient catalytic activity for esterification of succinic acid with ethanol. In a subsequent communication, the authors had used Glu-TSOH catalyst for fructose dehydration, reporting a maximum 91% HMF in DMSO solvent at 130° C. in 1.5 h. However, the effectiveness of the Glu-TsOH catalyst was not tested for the dehydration of fructose in aqueous medium and other difficult carbohydrates such as glucose, xylose, cellobiose etc.

Based on comparison of the catalytic activity of a series of solid acid catalysts having Lewis and Brønsted acidity for xylose dehydration in aqueous medium, it has been concluded that a high ratio of Brønsted to Lewis acid sites is desirable for effective catalysis. With the objective of investigating the role of Lewis and Brønsted sites in solid acid catalysts, disclosed herein is the synthesis and characterization of a new sulfonated carbonaceous material having both Brønsted acidic sulfonic acid group and Lewis acidic sites. The present disclosure disclosed herein also describes the catalytic effectiveness of the sulfonated carbonaceous material for the conversions of glucose, xylose, cellobiose and sucrose to the corresponding furfurals in aqueous medium using methyl tetrahydrofuran (MeTHF) as an organic phase in a biphasic system for extracting furfurals into the organic phase. Some reactions were also carried out in DMSO, DMA-LiCl (10 wt % LiCl) for comparison purposes.

EXAMPLE 1

Biomass Oxygenate Conversion to Hydrocarbons Using a High Pressure Reactor and Hydrodeoxygenation Catalyst Experimental Data
Lignin Derived Compound Dihydroeugenol:
100% conversion of dihydroeugenol was achieved in a fixed-bed, plug-flow, vapor-phase reactor with >97% yield of the hydrocarbon propylcyclohexane at 350 psi hydrogen partial pressure, 300° C., and a weight hourly space velocity of 5.1 (WHSV, gram dihydroeugenol·grams catalyst)$^{-1}$·hr$^{-1}$ using the 5% PtMo(1:1)/MWCNT catalyst.

Cellulose:
100% conversion of cellulose to hydrocarbons was achieved in a lab-scale, high-pressure, fast-hydropyrolysis reactor coupled to a second-stage, fixed-bed, vapor-phase catalytic hydrodeoxygenation (HDO) reactor. A yield of approximately 36% (on carbon basis) was obtained of C4-C6 hydrocarbon products from feed cellulose at 392 psi total pressure, 363 psi hydrogen partial pressure, fast-hydropyrolysis temperature of 480° C., HDO reaction temperature of 350° C., and a weight hourly space velocity of 12 (WHSV, gram cellulose·grams catalyst)$^{-1}$·hr$^{-1}$ using the 5% PtMo(1:1)/MWCNT catalyst.

Cellulose:
100% conversion of cellulose to hydrocarbons was achieved in a micro-scale, semi-batch reactor coupled to a fixed-bed HDO reactor. A yield of approximately 50% (on carbon basis) was obtained of C4-C6 hydrocarbon products from feed cellulose at 350 psi total pressure, approximately 350 psi hydrogen partial pressure, fast-hydropyrolysis semi-batch reactor temperature of 500° C., HDO reactor temperature of 300° C., and catalyst to feed ratio of approximately 20:1 using the 5% PtMo(1:1)/MWCNT catalyst.

Sorghum:
100% conversion of sorghum biomass to hydrocarbons was achieved in micro-scale, semi-batch reactor coupled to a fixed-bed HDO reactor. Approximately 40% yield (on carbon basis) was obtained of C4-C6 hydrocarbon products from feed sorghum at 350 psi total pressure, approximately 350 psi hydrogen partial pressure, fast-hydropyrolysis semi-batch reactor temperature of 500° C., HDO reactor temperature of 300° C., and catalyst to feed ratio of approximately 20:1 using the 5% PtMo(1:1)/MWCNT catalyst.

EXAMPLE 2

Hydrodeoxygenation

Materials and Methods
Chemicals:
Pd/C (5 wt %) was purchased from Strem Chemicals (Newburyport, Mass.). 4-Allyl-2,6-dimethoxyphenol (98% purity) was purchased from Alfa Aesar (Ward Hill, Mass.). Isoeugenol, eugenol, 2-methoxy-4-propylphenol (all >98% purity) and ammonium formate (>99% purity) were purchased from Sigma-Aldrich (St. Louis, Mo.). 2-Methoxy-4-methylphenol (98% purity) and methylparaben (>99% purity) were obtained from TCI America (Portland, Oreg.). High-performance liquid chromatography—mass spectrometry (HPLC/MS) grade water and acetonitrile were purchased from Fisher Scientific (Pittsburgh, Pa.). All chemicals were used without further purification. A Zorbax SB-C18 column (4.6×250 mm, 5 μm particle size) was purchased from Agilent Technologies (Santa Clara, Calif.). 2,6-Dimethoxy-4-propylphenol was synthesized as outlined below.

Preparation of 2,6-Dimethoxy-4-propylphenol 2,6-Dimethoxy-4-propylphenol was synthesized through the hydrogenation of the side chain of 4-allyl-2,6-dimethoxyphenol. 4-Allyl-2,6-dimethoxyphenol was dissolved in a suspension of Pd/C (5 wt %, 105 mg) in 15 mL MeOH (1.945 g, 10.1 mmol). The reaction mixture was placed in a stainless steel Parr reactor, pressurized, preferably, with 34 bar H$_2$ (though the reaction can be conducted in a hydrogen pressure range of 10-40 bar) and heated at 60° C. for 3 h. Pd/C was removed by filtration and methanol was removed in vacuo to yield 2,6-dimethoxy-4-propylphenol as a colorless oil. The reaction product was further purified on a silica column with mobile phase of 17% ethyl acetate and 83% hexanes. [$^1$H]NMR (CDCl$_3$) δ0.93 (t, 3H, CH$_3$), 1.61 (s, 2H, CH$_2$), 2.50 (t, 2H, CH$_2$), 3.85 (s, 6H, OCH$_3$), 5.42 (s, 1H, OH), 6.39 (s, 2H, ArH).

Biomass Preparation
Biomass was first milled to pass through a 40 mesh screen. Biomass was washed with consecutive water and ethanol soxhlet extractions following the LAP Determination of Extractives in Biomass procedure. Following soxhlet extraction, biomass was dried and subjected to moisture analysis using a Mettler Model HB43 Halogen Moisture Analyzer.

Determination of Lignin Content in Washed Biomass
DFRC:
Composition of lignin was determined by derivatization followed by reductive cleavage (DFRC) analysis, results of which are summarized in Table 3. Briefly, cell wall samples were dissolved in a acetyl bromide/acetic acid solution, containing 4,4'-ethylidenebisphenol as an internal standard. The reaction products were dried down using nitrogen gas, dissolved in dioxane/acetic acid/water (5/4/1, v/v/v), reacted with Zn dust, purified with C-18 SPE columns (SUPELCO), and acetylated with pyridine/acetic anhydride (2/3, v/v). The lignin derivatives were analyzed by gas chromatography/flame ionization detection using response factors relative to the internal standard of 0.80 for p-coumaryl alcohol peracetate, 0.82 for coniferyl alcohol peracetate, and 0.74 for sinapyl alcohol peracetate.

TABLE 3

DFRC analysis of lignin composition for each of the biomass samples

| Lignin Type | Poplar WT-717 | Poplar WT-NM-6 | Poplar WT-LORRE | Poplar 717-0998 | Poplar 717-F5H | WT-Lodgepole Pine | WT-White Birch | WT-Eucalyptus |
|---|---|---|---|---|---|---|---|---|
| H (mg) | 9.64 | 8.98 | 7.34 | 3.44 | 17.80 | 5.17 | 12.58 | 2.51 |
| G (mg) | 80.15 | 84.20 | 90.93 | 84.83 | 48.65 | 118.99 | 75.66 | 117.71 |
| S (mg) | 92.88 | 115.41 | 86.72 | 6.52 | 182.38 | 0.00 | 84.44 | 225.99 |

ABSL:

Each biomass was also subjected to Acetyl Bromide-soluble Lignin ("ABSL") treatment to estimate the lignin content (Table 4 summarizes the ABSL analysis). The dried samples (5-1 mg), weighed to the nearest 0.01 mg, were added to a 10 mL glass tube with 2.5 mL of 25% acetyl bromide in acetic acid. The tubes were tightly sealed with Teflon lined caps and a stir bar was added. Tubes were stirred at 70° C. for 30 min to 2 h (until the wall tissue is completely dissolved). After cooling the tubes to room temperature, the samples were transferred using acetic acid to a 10 mL volumetric flasks containing 2 mL 2M NaOH. The tubes were rinsed with acetic acid to complete the transfer. 0.35 mL 0.5 M (34.745 mg/mL) hydroxylamine hydrochloride (freshly prepared) was added to the volumetric flasks which were then made up to 10 mL with acetic acid. Inverted several times, the volume will decrease after inversion. The absorbance of the solutions was read at 280 nm.

TABLE 4

Acetylbromide soluble lignin content analysis (ABSL)

| Biomass Type | mg ABSL/g CW | % ABSL |
|---|---|---|
| Poplar WT-717 | 160 | 19 |
| Poplar NM-6 | 159 | 18 |
| Poplar WT-LORRE | 172 | 19 |
| Poplar 717-0998 (Low S Poplar) | 161 | 19 |
| Poplar 717-F5H (High S Poplar) | 174 | 20 |
| WT-Lodgepole Pine | 283 | 31 |
| WT-White Birch | 136 | 16 |
| WT-Eucalyptus | 215 | 24 |

General In Situ Generated Catalyst Reactions:

In a typical experiment: 1.0 g of biomass, Pd/C (5 wt %), $ZnCl_2$ (5-10 wt %), methanol (30 mL), and glass stir bar were added to a stainless steel Parr reactor, which was subsequently sealed. While stirring the mixture was purged with UHP grade $H_2$ for ~1 min., then pressurized with $H_2$ (500 psi, 34 bar). The mixture was heated to 225° C. This temperature was maintained for ca. 12 h. The reaction was terminated by removing the heat and cooling the reactor to room temperature (caution should be exercised when handling and venting the reactor; Pd/C is pyrophoric). The reaction mixture Parr was filtered to remove Pd/C and remaining solid biomass residue. This Pd/C/biomass mixture was washed with additional MeOH and the filtrate was collected and diluted in a volumetric flask. This solution was analyzed by GC-FID and HPLC/MS as described below to determine amounts of methoxypropylphenols.

Determination of Carbohydrates

Liquid Fraction:

To determine sugar content in the methanol fraction, 20 mL of $H_2O$ was added to 10 mL methanol and the resulting solution extracted 3 times with 20 mL of $Et_2O$ in each extraction to remove small organic fragments and aromatics. The methanol was then removed under reduced pressure. The carbohydrates in the water layer were quantified using a LAP sulfuric acid digestion method previously developed by Templeton et al. The results are tabulated in Table 5.

TABLE 5

Sugar content of the MeOH fraction after extraction of lignin. 1000 mg of raw biomass was used in each reaction.

| Biomass Type | Glucans (mg) | Xylans (mg) | Arabinans (mg) | Total Sugar (mg) |
|---|---|---|---|---|
| Poplar WT-717 | 17 | 52 | 8 | 77 |
| Poplar NM-6 | 23 | 78 | 5 | 106 |
| Poplar WT-LORRE | 61 | 55 | 4 | 71 |
| Poplar 717-0998 (Low S Poplar) | 24 | 80 | 5 | 109 |
| Poplar 717-F5H (High S Poplar) | 16 | 68 | 5 | 89 |
| WT-Lodgepole Pine | 30 | 85 | 5 | 118 |
| WT-White Birch | 24 | 42 | 4 | 70 |
| WT-Eucalyptus | 38 | 44 | 3 | 85 |

Solid Residue:

The remaining cellulosic residue for each biomass was collected on filter paper then dried. The moister content of each sample was measured and the carbohydrates in the samples were quantified using a LAP sulfuric acid digestion method previously developed by Crocker et al.

HPLCIMS Analysis

Instrumentation.

All analyses were performed using a Thermo Scientific linear quadrupole ion trap (LQIT)—Fourier transform ion cyclotron resonance (FT-ICR; 7 T magnet) mass spectrometer coupled with a Surveyor Plus HPLC. The HPLC system consisted of a quaternary pump, autosampler, thermostatted column compartment, and photodiode array (PDA) detector. The LQIT was equipped with an ESI source. HPLC eluent (flow rate of 500 µL/min) was mixed via a tee connector with a 10 mg/mL sodium hydroxide water solution (flow rate of 0.1 µL/min) and connected to the ion source. This allows for efficient negative ion generation by ESI. The LQIT-FT-ICR mass spectrometer was operated using the LTQ Tune Plus interface. Xcalibur 2.0 software was used for HPLC/MS data analysis. Automated gain control was used to ensure a stable ion signal. A nominal pressure of $0.65 \times 10^{-5}$ Torr, as read by an ion gauge, was maintained in the higher pressure LQIT vacuum manifold and $2.0 \times 10^{-10}$ Torr in the FT-ICR vacuum manifold, as read by an ion gauge.

High-Performance Liquid Chromatography/High-Resolution Tandem Mass Spectrometer:

All samples were introduced into the HPLC/MS via an autosampler as a full-loop injection volume (25 µL) for high reproducibility. 1 mg/L ammonium formate in water solution (A) and 1 mg/mL ammonium formate in acetonitrile solution (B) were used as the mobile phase solvents. Ammonium formate was used to encourage negative ion production. A nonlinear, two-slope gradient was used (35% A and 65% B at 30.00 min to 5% A and 95% B at 55.00 min). The column was placed in a thermostatted column compartment that maintained the column at a temperature of 30° C. to increase the reproducibility of the retention times and peak widths. The PDA detector for HPLC was set at 280 nm. The exact conditions used for ionization of the analytes and injection of the ions into the mass spectrometer were optimized using a stock solution of 2-methoxy-4-propylphenol in a 0.15 mg/mL NaOH 50:50 acetonitrile/water solution. All ion optics were optimized using the automated tuning features of the LTQ Tune Plus interface. The ESI probe position was optimized manually for optimal signal. The following ESI conditions were used: sheath gas pressure 60 (arbitrary units), auxiliary gas pressure 30 (arbitrary units), sweep gas pressure 0 (arbitrary units), and spray voltage 3.50 kV. For the analysis of lignin conversion products, data-dependent scans were used. Data-dependent scanning involves the instrument automatically selecting the most abundant ions from the ion source, one after each other, for further experiments. This allows for separate MS acquisitions to be performed simultaneously for the same ions in the two different mass analyzers of the LQIT-FT-ICR wherein the higher duty-cycle LQIT performs tandem mass spectral acquisitions for the selected ions while the lower duty-cycle FT-ICR carries out high-resolution measurements for elemental composition determination for the same ions. A resolving power of 400,000 at m/z 400 was used in the FT-ICR. The $MS^2$ experiments involve the isolation (using a mass/charge ratio window of 2 Th) and fragmentation of selected ions formed upon negative ion-mode ESI spiked with NaOH. The ions were kinetically excited and allowed to undergo collisions with helium target gas for 30 ms at a q value of 0.25 and at a normalized collision energy (24) of 40%. The most abundant product ion formed in the $MS^2$ experiments was subjected to a further stage of ion isolation and fragmentation ($MS^3$). Table 6 summarizes the data for the sugar content of the remaining cellulosic solid residue after lignin conversion over Zn/Pd/C as determined via acid hydrolysis with HPLC analysis. The results are shown in Table 6.

TABLE 6

Sugar content of the remaining cellulosic solid residue after lignin conversion over Zn/Pd/C as determined via acid hydrolysis with HPLC analysis.

| Biomass Type | Residue Mass (mg)[a] | Glucan (mg) | Xylan (mg) | Arabinan (mg) | Total Sugars (mg) | Total Sugar % |
|---|---|---|---|---|---|---|
| Poplar WT-717 | 555 | 383 | 29 | 4 | 416 | 75 |
| Poplar WT-LORRE | 627 | 433 | 57 | 4 | 504 | 80 |
| Poplar 717-0998 (Low S Poplar) | 572 | 468 | 38 | 4 | 510 | 89 |
| Poplar 717-F5H (High-S Poplar) | 572 | 430 | 49 | 4 | 573 | 84 |
| Poplar WT-NM-6 | 477 | 261 | 21 | 4 | 286 | 60 |
| Lodgepole Pine WT | 546 | 398 | 22 | 4 | 424 | 78 |
| White Birch WT | 475 | 365 | 0 | 4 | 369 | 78 |
| Eucalyptus WT | 506 | 429 | 0 | 4 | 433 | 86 |

[a]Mass of the residue excluding Pd/C catalyst and moisture.

Quantitation of Aromatic Products from Lignin Conversion:

Standard solutions, each containing 2,6-dimethoxypropylphenol, 2-methoxy-4-propylphenol, methylparaben, eugenol, and isoeugenol, were made from 1.0 mM stock solutions and diluted to a final volume of 1.0 mL with the following final concentrations: 0.005, 0.010, 0.050, 0.10, and 0.15 mM. 2-Methoxy-4-methylphenol was used as the internal standard (0.1 mM) and was added into each of the five standard solutions. A full-loop injection was performed for each standard solution; thus, a total volume of 25 μL was injected onto the column. After separation, the ion chromatograms for deprotonated 2,6-dimethoxypropylphenol, 2-methoxy-4-propylphenol, methylparaben, eugenol, isoeugenol and 2-methoxy-4-propylphenol were extracted from measured mass spectrometric data by Thermo Xcalibur Quan Browser software and used to create the calibration curves. Table 7 summarizes the results of HPLC/MS quantitation of all soluble aromatic/phenolic products from lignin conversion and HDO over Zn/Pd/C catalyst in MeOH.

TABLE 7

HPLC/MS quantitation of all soluble aromatic/phenolic products from lignin conversion and HDO over Zn/Pd/C catalyst in MeOH.[a]

| Biomass Type | Methylparaben (mg)[b] | 2,6-Dimethoxy-4-propylphenol (mg) | Dihydroeugenol (mg) | Removed Oxygen (mg)[c] |
|---|---|---|---|---|
| Poplar WT-717 | 5.4 | 49.4 | 21.9 | 2.3 |
| Poplar NM-6 | 6.7 | 62.5 | 30.5 | 3.0 |
| Poplar WT-LORRE | 26.2 | 56.1 | 46.0 | 3.3 |
| Poplar 717-0998 (Low S Poplar) | 1.4 | 5.1 | 44.3 | 1.6 |
| Poplar 717-F5H (High S Poplar) | 3.2 | 59.4 | 12.1 | 2.3 |
| Lodgepole Pine WT | n/a | n/a | 56.5 | 1.8 |
| White Birch WT | n/a | 54.0 | 26.3 | 2.6 |
| Eucalyptus WT | n/a | 80.0 | 34.5 | 3.7 |
| Poplar WT-LORRE no $ZnCl_2$ | 6.8 | 8.3 | 6.6 | 0.5 |
| Poplar WT-LORRE no Pd/C | 15.2 | 0 | 0 | 0 |
| Poplar WT-LORRE no $H_2$ | 8.4 | 1.4 | 3.7 | 0.15 |

[a]Based on 1,000 mg of starting intact biomass.
[b]Methylparaben is a quantifiable aromatic product that is extracted during catalysis.
[c]Calculated using the number of moles of products generated based on the fact that two atoms of O are removed for every mole of product.

Calculating % Yield

The % yield of products is based on the total mass of the products and removed O divided by the mass of the lignin content of each sample as shown in the following Equation 1.

$$\% \text{ yield} = \frac{\text{dihydroeugenol (mg)} + 2,6-\text{dimethoxy}-4-\text{propyl phenol (mg)} + \text{removed } O}{\text{initial weight of biomass (mg)} \times ABSL \text{ lignin } \%} \times 100 \quad \text{Equation 1}$$

Pyrolysis of the Solid Biomass Cellulosic Residue

Figure 7:
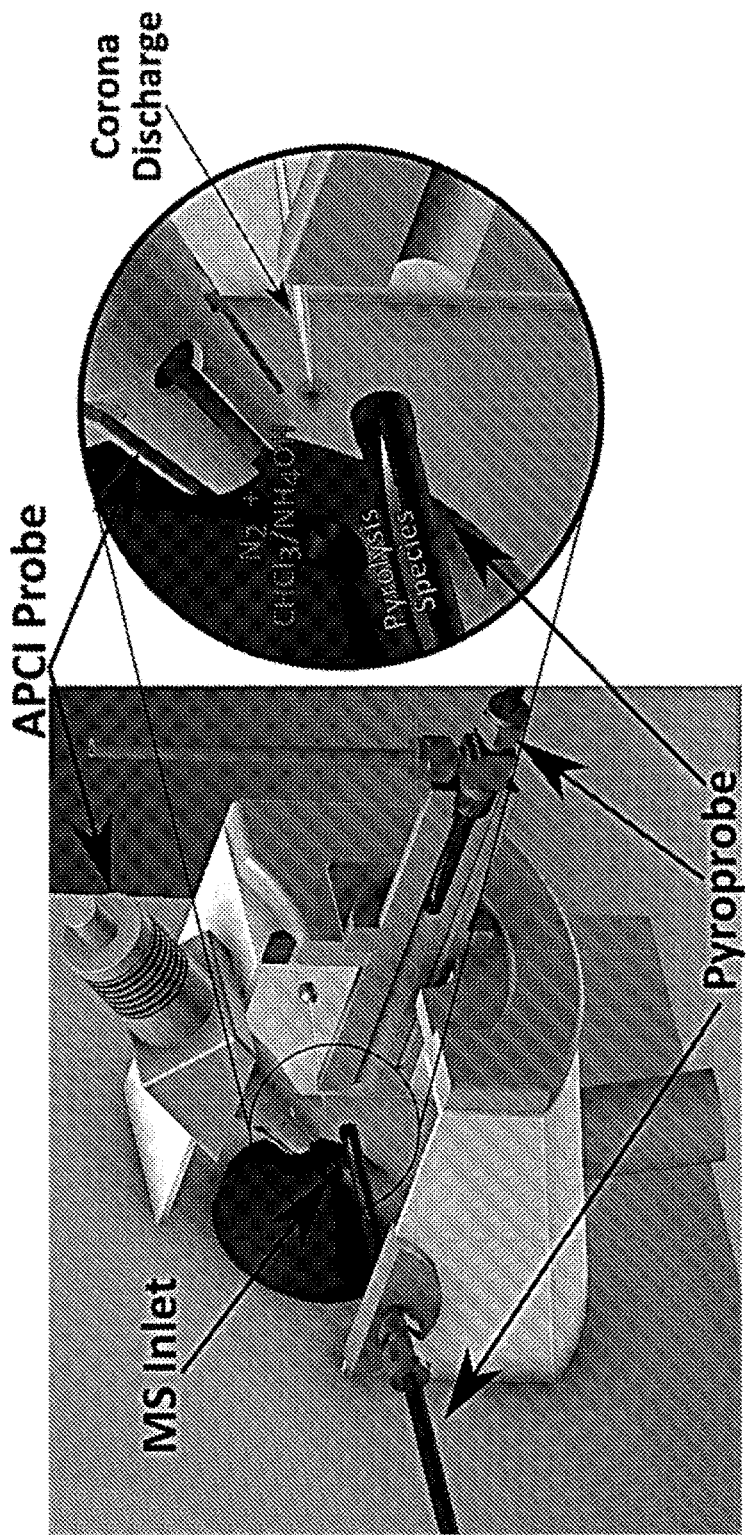
FIG. 7 is a schematic of the pyrolysis mass spectrometer setup.

Instrumentation:

Pyrolysis experiments were performed using a Pyroprobe 5200 HP supplied by CDS Analytical (Oxford, Pa.). The pyroprobe is equipped with a resistively heated platinum coil surrounding a quartz tube capable of heating at up to 20,000° C. $s^{-1}$. Sample was loaded on the inside of the quartz tube and then pyrolyzed with a heating rate of 1000° C. $s^{-1}$ at a temperature of 600° C. for 3 seconds. The pyrolysis products were then immediately quenched in a 100° C. region where they were ionized via either positive or negative mode Atmospheric Pressure Chemical Ionization (APCI). A schematic of the pyrolysis mass spectrometer setup is depicted in FIG. 7. Pyrolysis product characterization was performed using a Thermo Scientific (Waltham, Mass.) LTQ linear quadrupole ion trap (LQIT) coupled with a Finnigan Surveyor Liquid Chromatograph (LC) MS Pump Plus.

High Resolution Tandem Mass Spectrometry:

Pyrolysis product ionization was achieved with the aid of dopants infused into the APCI source through the APCI probe. The corona discharge was operated at 3000 V with a discharge current of 4 µA. In both positive and negative mode APCI, a 50:50 (v/v) solution of ammonium hydroxide: water was tee infused with a 50:50 (v/v) solution of methanol:water. In positive mode APCI the flow rates were 3 µL $min^{-1}$ for the ammonium hydroxide:methanol solution and 300 µL $min^{-1}$ for the methanol:water solution. With positive mode APCI the expected ionization adducts are either analyte protonation ($[M+H^+]^+$) or analyte ammoniation ($[M+NH_4^+]^+$). On the other hand, in negative mode APCI the flow rates were 1 µL $min^{-1}$ for the ammonium hydroxide:methanol solution and the same flow rate of 300 µL $min^{-1}$ for the methanol:water solution. With negative mode APCI the expected ionization adduct is deprotonation ($[M-H^+]-$).

EXAMPLE 3

Solid Acid Catalyst

Catalyst Synthesis

The biorenewable solid Ti-containing carbonaceous acid catalyst, Glu-TsOH-Ti, was prepared via thermal treatment of p-toluenesulfonic acid (TsOH), glucose and titanium(IV) isopropoxide at 180° C. In a specific preparation, 2 g glucose, 2 g TsOH and 0.5 g titanium iospropoxide were mixed well and transferred in a 25 mL Teflon-sealed autoclave, and maintained at 180° C. for 24 h. The obtained black material was grinded to powder using mortar-pestle, washed with water and ethanol and oven-dried at 80° C. Other catalysts in this embodiment includes the Glu-TsOH-Ti material that can be prepared by varying the ratio of p-toluenesulfonic acid and titanium(IV) isopropoxide in the range of 0.25-5.0.

Instrumentation

Powder X-ray diffraction (PXRD) patterns were recorded on a Bruker D-8 Advance diffractometer operated at 40 kV and 40 mA and calibrated with a standard silicon sample, using Ni-filtered Cu Kα ($\lambda$=0.15406 nm) radiation. JEOL JEM 6700F field emission scanning electron microscope (SEM) was used for the determination of morphology of powder samples. The pore structure was explained by a JEOL JEM 2010 transmission electron microscope (TEM) operated at an accelerating voltage of 200 kV. Fourier transform infrared (FT IR) spectrum of the catalyst material was recorded on a Perkin-Elmer Lambda-25 spectrophotometer. Variable temperatures FT IR spectra of the pyridine adsorbed sample were recorded on KBr pellet by using Perkin-Elmer Spectrum 100 spectrophotometer. For pyridine IR studies, the sample was allowed to contact with pyridine vapor in a closed vessel at 75° C. for 2 hr and then recorded the desorption spectrum at elevated temperatures.

Nitrogen adsorption/desorption isotherms were obtained by using a Beckman Coulter SA 3100 Surface Area Analyzer at 77 K. Temperature programmed desorption (TPD) analysis of ammonia was conducted by using Micrometrics ChemiSorb 2720 in the temperature range of 100-700° C. which employed a thermal conductivity detector. For $NH_3$-TPD measurement, the sample was activated at 300° C. inside the reactor of the TPD furnace under helium flow for 4 hr. After cooling it to room temperature, ammonia was injected in the absence of carrier gas flow and the system was allowed to equilibrate. Helium gas was used to flush out the excess ammonia. The temperature was then raised in a programmable manner at a linear heating rate of 10° C. per min. AAS analysis of the sample was performed on Shimadzu AA-6300 atomic absorption spectrometer.

The microwave assisted conversions of all substrates were performed on a CEM Corporation Discover™ Microwave reactor at the standard operating frequency and 100 Watt power. HMF and furfural yields were measured by UV-visible spectrophotometric techniques using a Shimadzu UV-2501PC spectrophotometer. Yields of HMF and furfural in the product solutions were further validated by HPLC analysis on a Water HPLC instrument equipped with Waters 2487 PDA and 2414 refractive index detectors. $^1$H NMR spectra of HMF were recorded on a Bruker ARX 400 MHz instrument and NMR data were processed with XWinNMR software.

Conversion of Carbohydrates to HMF and Furfural

The dehydration reactions of carbohydrates were carried out by charging substrates, solvent and catalyst in a 10 mL microwave tube. The loaded microwave tube was then inserted into the microwave reactor pre-set to the desired temperature and reaction time. Upon completion of the allotted reaction time, the reactor was opened. The temperature of the reaction mass was cooled down to room temperature and the solution was filtered through a 0.22 µm cut off syringe filter (25 mm diameter) for analysis. In the case of biphasic solvent mediated reactions, both organic and aqueous phase were separately analyzed for quantification of furfural yield and carbohydrate conversion. The conversions of starting carbohydrate substrate were calculated from HPLC analysis data by determining unconverted substrate in the aqueous phase. For $^1$H NMR analysis, MeTHF was removed from the organic phase by rotary evaporation, and the organic oily product was dissolved in acetone-$d_6$. Dimethylformamide was used as an internal standard.

Recyclability Study of Glu-TsOH-Ti Catalyst

The recycling efficiency of the catalyst was determined for the dehydration of fructose as a representative reaction.

In this study, 0.2 mmol fructose, 22 mg catalyst, 2 mL MeTHF, and 1 mL water were charged in a 10 mL microwave tube. The tube was placed in the microwave reactor and the mixture was heated at 180° C. using 100 Watt microwave power for 60 min. After reaction, the tube was cooled down to room temperature and an aliquot was collected for analysis. The solid catalyst left in the tube was collected and re-used for three consecutive cycles by adding fresh substrate and solvent. Fresh catalyst was not added to compensate any loss of the catalyst during recovery. The yield of HMF was determined from each run.

Determination of HMF Yield:

By UV-Visible Spectrophotometric Method:

The UV-visible spectra of pure HMF and Ff solutions have distinct peaks at 284 nm and 268 nm with their corresponding extinction coefficient ($\epsilon$) values of $1.66 \times 10^4$ $M^{-1}$ $cm^{-1}$ and $1.53 \times 10^4$ $M^{-1}$ $cm^{-1}$, respectively. The mol percentage of furfurals in each of the reaction product was calculated from the measured absorbance values at respective $\lambda_{max}$ for HMF and Ff and the corresponding extinction coefficient values.[7] First, standard HMF and Ff solutions of 98-99% purity were separately analyzed for correlating the percentage of actual and calculated amount of HMF and Ff. Once good correlations were established, HMF product samples were run and the percentage of HMF and Ff yields were calculated. Repeated measurement of the same solution showed that the percentage of error associated with this measurement was in the range of ±5%.

By HPLC Method:

For water-MeTHF biphasic solvent mediated reactions, HPLC analyses of both organic and aqueous phases were performed separately. The organic phase was analyzed on Water HPLC instrument equipped with a Waters 152 pump, a XDB-$C_{18}$ column (Agilent), and a Waters 2487 PDA detector. A solution of 80% formic acid (0.1%) and 20% methanol was used as the mobile phase at a flow rate of 1 mL $min^{-1}$. HPLC analysis of the aqueous phase was performed on Waters 2695 Separations Module equipped with an Aminex HPX-87H column (300×7.8 mm) set at 65° C. and Waters 2414 refractive index detector for determination of unconverted carbohydrates as well as furfurals. A solution of 5% acetonitrile in sulfuric acid (0.005 M) was used as the mobile phase at a flow rate of 0.6 mL $min^{-1}$. The characteristic peaks for furfurals and unconverted carbohydrates in the product solutions were identified by their retention times in comparison with authentic samples. Each peak was integrated and the actual concentrations of glucose, fructose, xylose, furfural and HMF were calculated from their respective pre-calibrated plots of peak areas versus concentrations.

Material Synthesis and Characterization

Figure 8A:
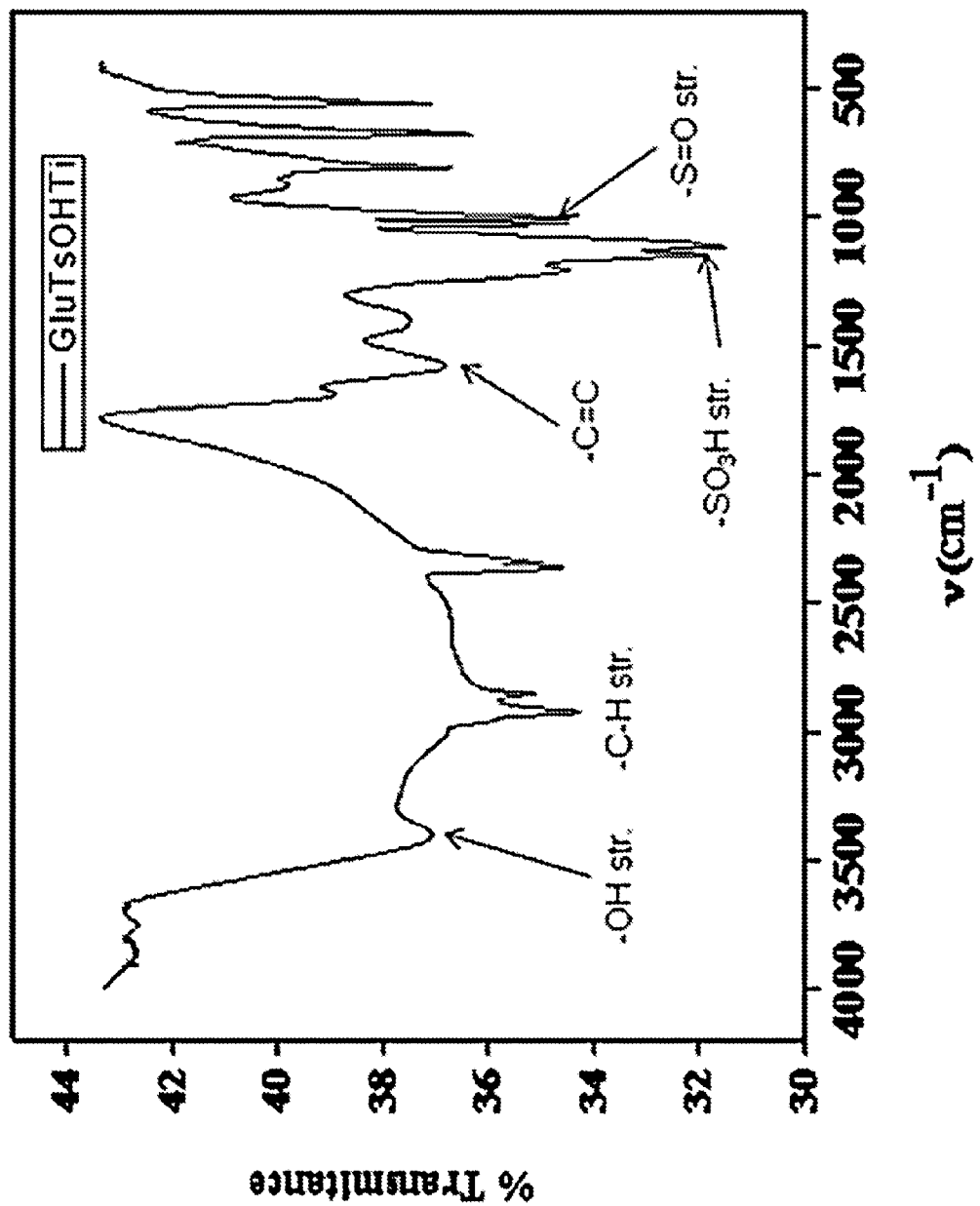
FIG. 8a shows the FT-IR spectrum of the Glu-TsOH catalyst.

FT-IR Study:

The FT-IR spectrum of Glu-TsOH-Ti catalyst is shown in FIG. 8a. It shows peaks at 1010, 1035, and ~1115 $cm^{-1}$ for —$SO_3H$ groups, indicating that Brønsted acidic sulfonic acid group was successfully incorporated into the carbon framework. The bands for —O—H stretching at ~3400 $cm^{-1}$, —C—H stretching at 2950-2875 $cm^{-1}$, —C=O stretching at ~1680 $cm^{-1}$, —C=C stretching at ~1610 $cm^{-1}$ were also observed.

Figure 8B:
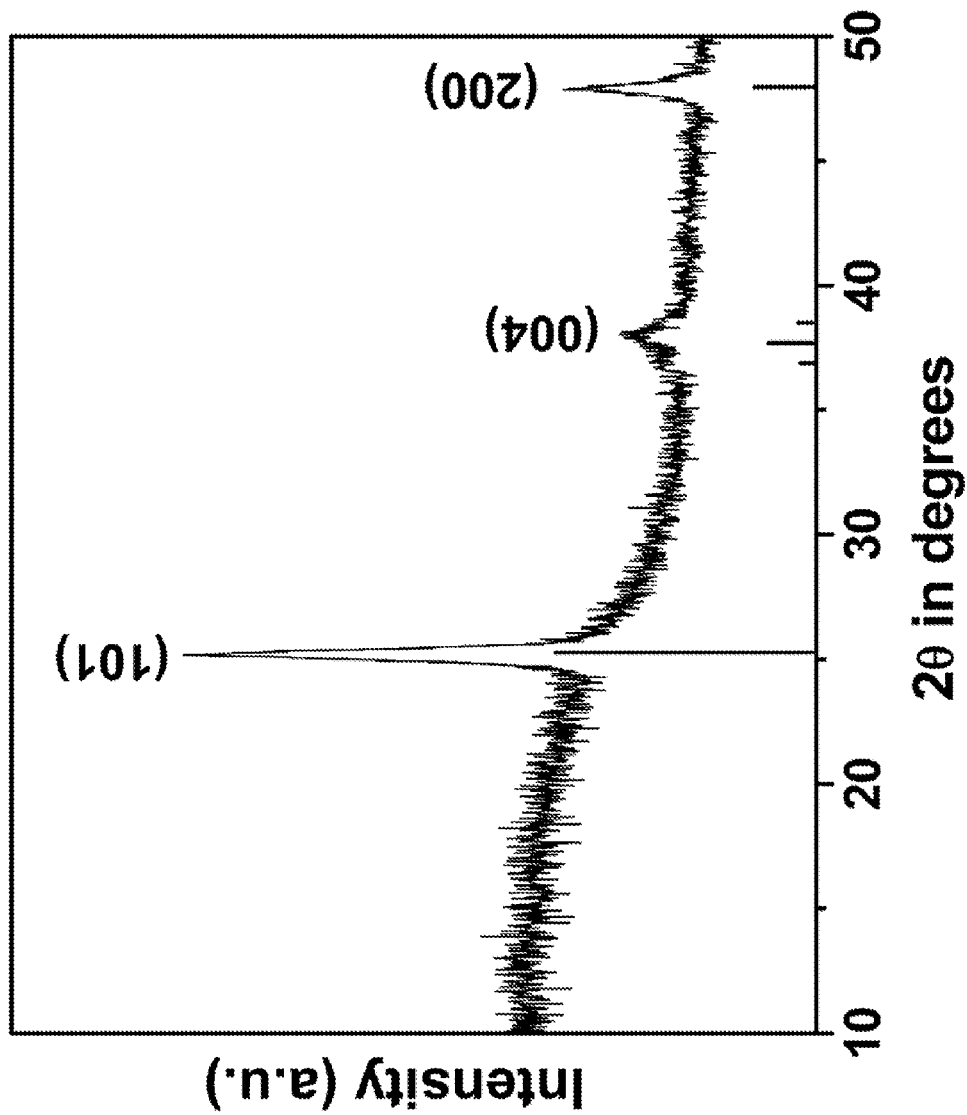
FIG. 8b is a wide angle XRD pattern of Glu-TsOH-Ti catalyst.
Figure 9A:
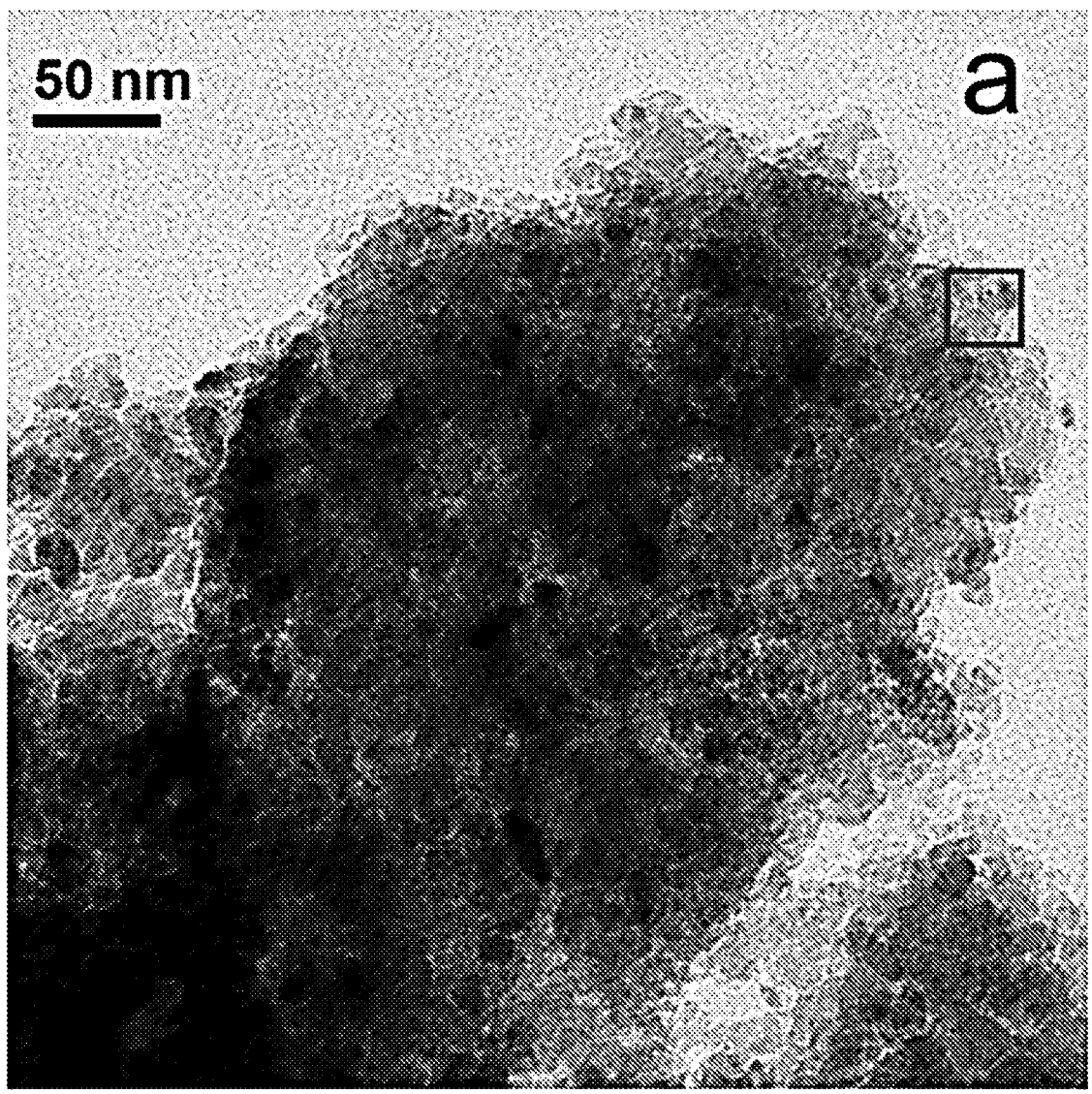
FIG. 9a is an HR TEM image of Glu-TsOH-Ti.
Figure 9B:
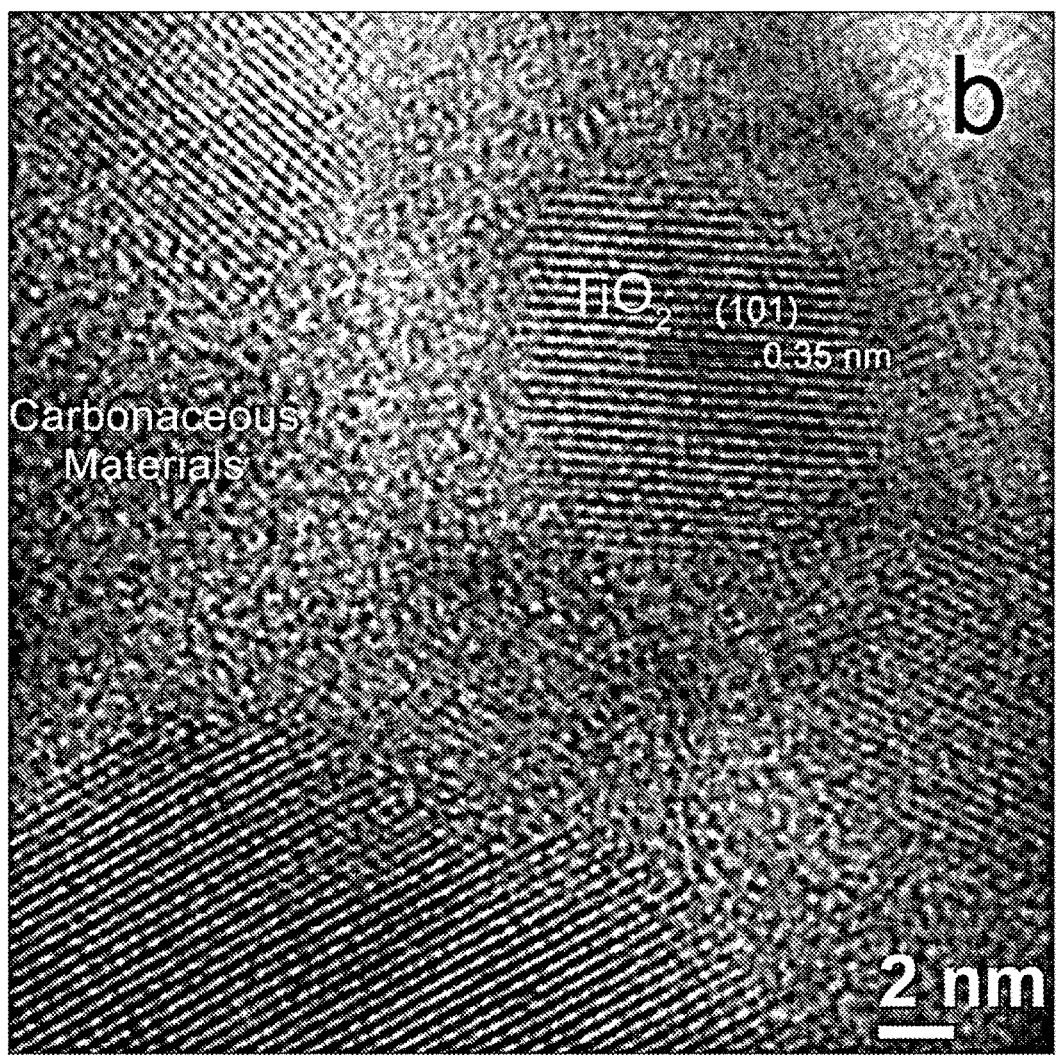
FIG. 9b is an HR TEM image of Glu-TsOH-Ti.

XRD Study:

The wide angle XRD pattern of Glu-TsOH-Ti catalyst (FIG. 8b) revealed that the material is crystalline and the major crystalline peaks at 2θ values of 25.3°, 37.8° and 48.0° correspond to anatase $TiO_2$ (101), (004), and (200) crystal planes (JCPDS File Card No. 21-1272). The crystalline planes corresponding to the peaks for anatase $TiO_2$ have been indexed in FIG. 8b. The presence of crystalline $TiO_2$ particles in the carbonaceous material was further studied by HRTEM analysis (see FIGS. 9a and 9b, which are HR TEM images of Glu-TsOH-Ti showing nanostructure of the material at different magnifications).

Figure 10A:
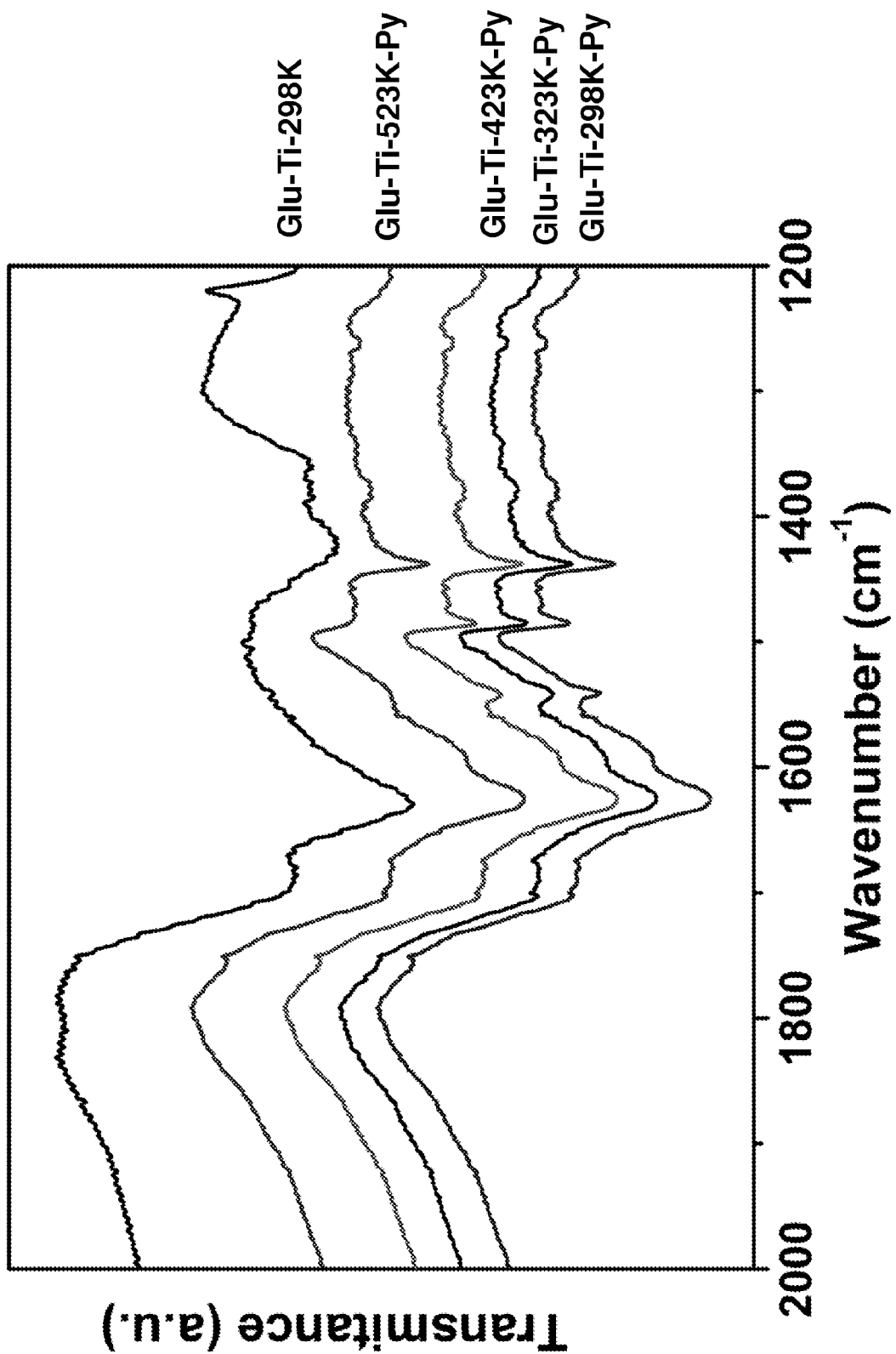
FIG. 10a depicts the pyridine desorbed FT-IR spectra for the Glu-TsOH-Ti catalyst at 298K, 323K, 423K, and 523K.
Figure 10B:
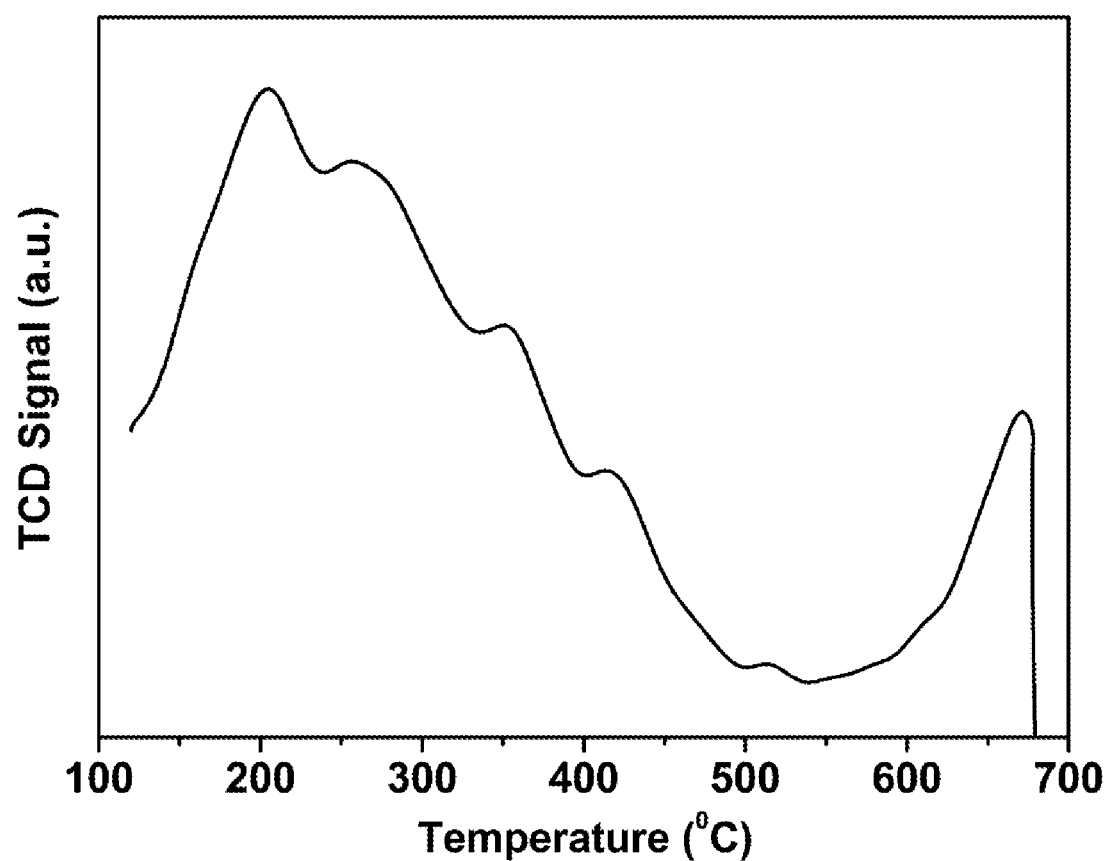
FIG. 10b shows the temperature programmed desorption of ammonia of the Glu-TsOH-Ti material.

Acidity Measurement:

Temperature programmed FT-IR spectroscopy is one of the most important analytical tools for characterizing the acidic property of the hybrid materials using pyridine as a Lewis base. As seen in FIG. 10a (which depicts the pyridine desorbed FT-IR spectra at 298K, 323K, 423K, and 523K), all the pyridine adsorbed Glu-TsOH-Ti samples have four characteristic adsorption bands at 1587 (broad), 1539 (sharp), 1487 (sharp) and 1438 (sharp) $cm^{-1}$. The band at 1438 $cm^{-1}$ could be attributed to the adsorbed pyridine at the Lewis acidic sites, whereas that at 1487 $cm^{-1}$ could be assigned for the overlap of the Brønsted and Lewis acid sites present in the sample. With increase in desorption temperature these bands showed very slow decrease in intensity due to removal of surface bound pyridine molecules from the Glu-TsOH-Ti surface. The adsorption bands at 1587 (broad) and 1539 (sharp) $cm^{-1}$ could be due to the presence of pyridinium ion (pyridine-Brønsted acid site complex) bound at the Brønsted acid sites of the —$SO_3H$ groups. At higher desorption temperature (523 K), these adsorption bands corresponding to the Brønsted acid sites disappear, suggesting moderately strong Brønsted acid strength in the Glu-TsOH-Ti material. Thus, the pyridine-IR result suggested the presence of considerably strong Brønsted and Lewis acid sites in our self-assembled Glu-TsOH-Ti material. Further, $NH_3$-TPD analysis of the Glu-TsOH-Ti material was conducted for quantifying surface acidity. The amount of ammonia desorbed in the temperature values of 178, 266 and 674° C. were taken as measures for weak, medium and strong acid sites with corresponding acid density values of 0.00821, 0.06278 and 0.02710 mmol $g^{-1}$, respectively (FIG. 10b). Out of total acid density of 0.1 mmol $g^{-1}$, strong acidic sites correspond to the Brønsted acidity, and week and medium acidic sites correspond to the Lewis acidity of the Glu-TsOH-Ti material.

Nanostructural Analysis:

A scanning electron microscopic image (FE-SEM) of Glu-TsOH-Ti sample (deposited in the supporting information) shows that the material is composed of spherical nanoparticles of dimension of ca. 40-60 nm. These spherical nanoparticles are almost uniform in size and self-assembled to form large spherical aggregated particles. Tiny nanoparticles and their spherical morphological feature could help with the diffusion of products from the active catalytic site during the reaction. Elemental mapping via *Energy Dispersive X-ray Spectroscopy* (EDS) in SEM confirmed the presence of both Ti and S in the material with their weight percentage of 10.2 and 4.5, respectively (deposited in the supporting information). Further, AAS analysis also showed the presence of 3.2 atomic % of Ti in the sample, which compares very well with 2.94 atomic % of Ti obtained from EDS.

Transmission electron microscopic images (HR-TEM) of Glu-TsOH-Ti sample (FIGS. 9a and 9b) at different magnifications show the plate-like particles of dimension 5-10 nm are self-assembled by forming self-aggregated (loose assembly) nanostructure. A close view of these figures revealed the interparticle porosity of these self-assembled particles is about 4.0 nm. The observed interparticle porosity was further evidenced from the results of $N_2$ sorption studies as discussed below.

Figure 11A:
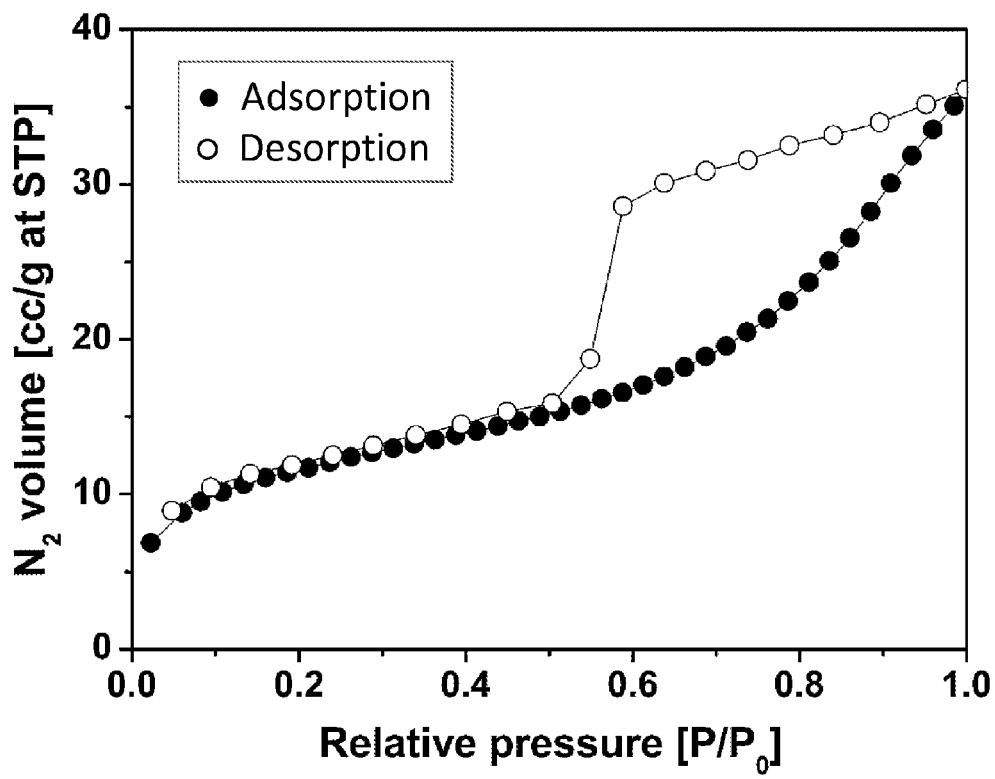
FIG. 11a shows the $N_2$ adsorption-desorption isotherm of the Glu-TsOH-Ti sample at 77 K (the (●) symbols represents adsorption and the (○) symbol represents desorption).
Figure 11B:
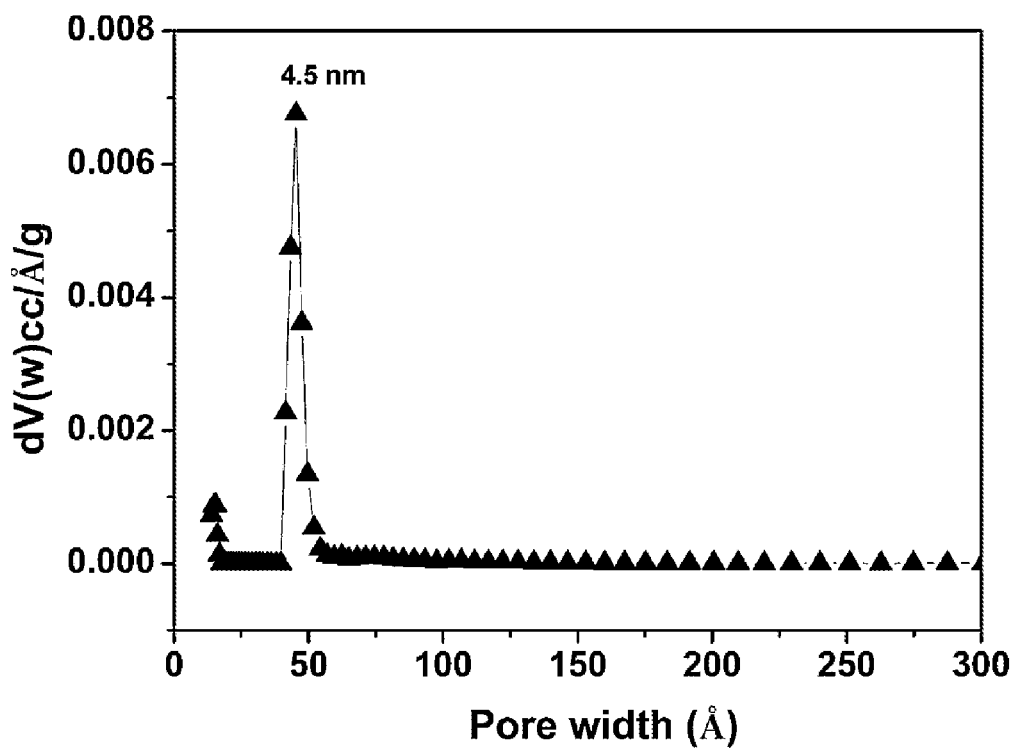
FIG. 11b shows the representative pore size distributions employing the nonlocal density functional theory (NLDFT).

N₂ Sorption Study:

Porosity and BET surface area of the Glu-TsOH-Ti material was investigated from the $N_2$ adsorption/desorption study at 77 K. The $N_2$ sorption isotherm of hydrothermally synthesized Glu-TsOH-Ti material is shown in FIGS. 11a and 11b (depicting N2 adsorption-desorption isotherm of: FIG. 11a, the Glu-TsOH-Ti sample at 77K; and FIG. 11b, representative pore size distributions employing the nonlocal density functional theory (NLDFT)). This isotherm can be classified as type IV isotherm with H2 hysteresis loop corresponding to the mesoporous materials based on their adsorption isotherm in low $P/P_0$. H2 hysteresis loop can be linked to narrow necks pores with wide bodies with the ascending boundary curve of the isotherm following a trajectory similar to that obtained with medium porosity adsorbents. BET surface area of Glu-TsOH-Ti material was 42.5 $m^2$ $g^{-1}$ with pore volume of 0.0543 $ccg^{-1}$. In this isotherm, between $P/P_0$ of 0.04-0.70 the $N_2$ adsorption gradually increases. The pore size distribution of the sample, measured using the Non Local Density Functional Theory (NLDFT) method (using $N_2$ adsorption on silica as a reference), suggested that the Glu-TsOH-Ti material has an average pore of ca 4.5 nm.

Catalysis for HMF Production

Several experiments were designed for studying the catalytic dehydration of monosaccharides (fructose, glucose, sucrose, xylose and xylulose) and disaccharides (sucrose, and cellobiose) to HMF and Ff under various experimental conditions, such as nature of solvents, nature of substrates, catalyst loadings, reaction temperatures and time. The carbohydrate substrates containing hexose sugars, such as fructose, glucose, sucrose and cellobiose were dehydrated to HMF, while xylose and xylulose substrates containing pentose units formed Ff as the desired product.

Figure 12A:
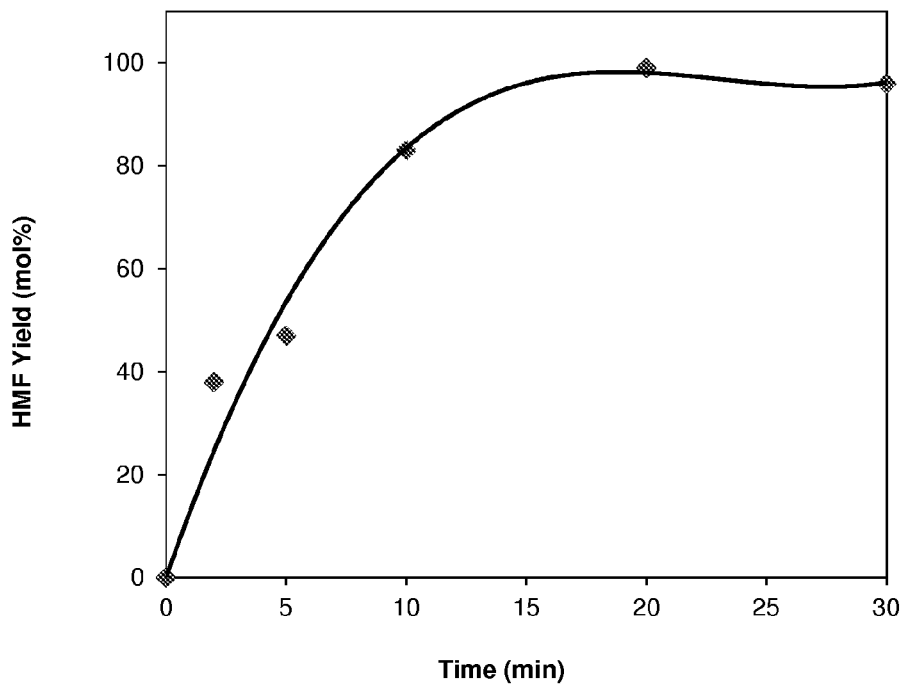
FIG. 12a shows the time dependent formation of HMF from fructose dehydration with the Glu-TsOH-Ti catalyst.

A preliminary reaction for dehydration of 0.56 mmol fructose with 50 mg Glu-TsOH-Ti catalyst was carried out in 4 mL DMSO at 150° C. Analysis of aliquots, collected at different times during the reaction progress, showed an increase in HMF yield as a function of reaction time. A maximum 99 mol % HMF yield was achieved within 20 min (FIG. 12a) with an appearance of a pale yellow color in the solution. The pale yellow color in the product solution is an indication that black colored human oligomer did not form as a by-product under these conditions. Clean ¹H NMR spectrum of the product solution in acetone-$d_6$ (deposited in the supporting information) further confirmed the purity of HMF, as proton signals for the side products, levulinic and formic acids, were not present in the NMR spectrum. Previous work on dehydration of 2.8 mmol fructose with 400 mg Glu-TsOH catalyst in 6 mL DMSO at 130° C. reported 91% HMF in 1.5 hr. A rough comparison of the reported data with the Glu-TsOH catalyst having only Brønsted acidity of 2.0 mmol $g^{-1}$ and our result using significantly less amount of Glu-TsOH-Ti catalyst suggests that the catalytic activity of our carbonaceous material, containing both Brønsted acidity (0.027 mmol $g^{-1}$) and Lewis acidity (0.071 mmol $g^{-1}$), is superior, though a thorough comparison cannot be made because of differences in heating conditions (oil bath heating versus microwave) and temperatures. Although total acidity of our Ti-containing carbonaceous material is significantly lower than the reported Ti-free carbonaceous catalyst, the superior HMF selectivity in the product by the Ti-containing catalyst can be explained by its Lewis acidic sites as well as higher surface area (42.5 $m^2$ $g^{-1}$) than the Ti-free material (<1 $m^2$ g-1). Previous literature report showed that combined Lewis acidic metal chloride and HCl catalyzed reaction produced HMF with significantly higher selectivity than that obtained using HCl catalyst alone. Additionally, higher pore volume of the Ti-containing catalyst (4.5 nm) may also favor the formation of high selective HMF, although pore volume of the reported Ti-free carbonaceous catalyst was not given.

Figure 12B:
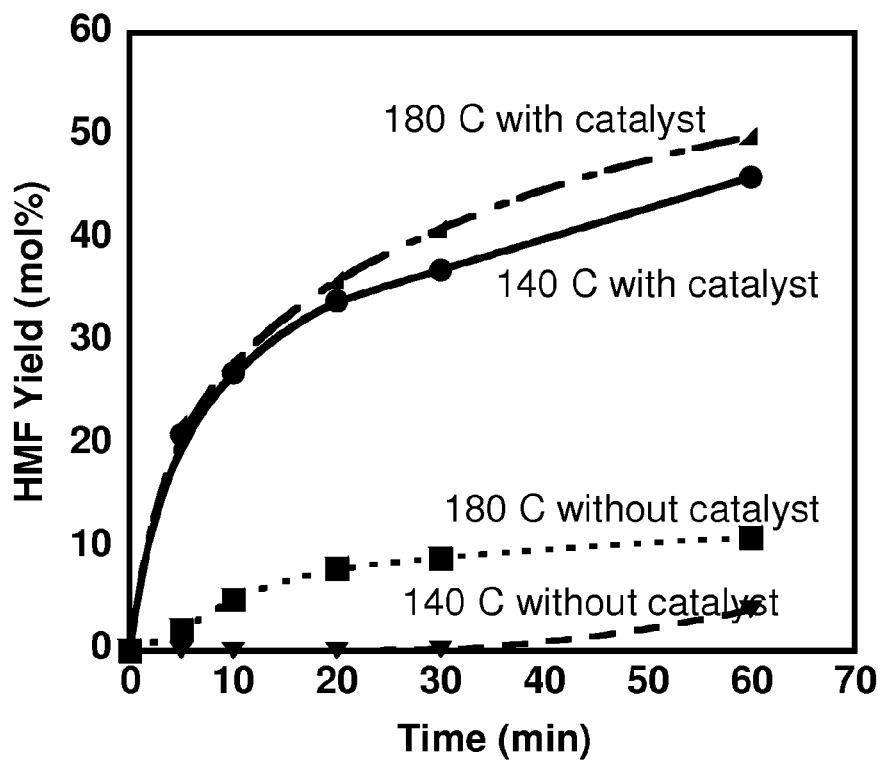
FIG. 12b shows the time dependent formation of HMF from glucose dehydration with and without the Glu-TsOH-Ti catalyst in DMSO.

The effectiveness of the Glu-TsOH-Ti catalyst was further tested for difficult substrates, such as glucose, whose dehydration is known to occur via the isomerization of glucose to fructose. Using 2 mL DMSO as a solvent, the dehydration of 0.28-0.31 mmol of glucose with 20-26 mg of catalyst was carried out at two different temperatures: 140° C. and 180° C. Referring to FIG. 12b, the results as plotted show an increase in HMF yield upon increasing the reaction time from 5 min to 30 min at both temperatures. However, the rate of formation of HMF at two different temperatures did not differ significantly, which could be due to the loss of HMF in the form of humin oligomer at higher temperature. It was also observed that the solution color turned from brown to black within 5-10 min, indicating the formation of a significant amount of humin by-product. Although the yield of humin was not quantified, such humin formation was not observed in fructose dehydration reaction at 150° C. in the same solvent (DMSO). This result suggests that the oligomerization of HMF occurs preferably with glucose. The blank experiments for glucose dehydration under comparable reaction condition showed that HMF yield without catalyst at 180° C. was only about 9% in 60 min, whereas at 140° C. the yield of HMF in control experiments was quite small (FIG. 12b).

As noted above, the yield of HMF from fructose dehydration reaction in DMSO was impressive; the major challenge, however, is the product extraction and purification from DMSO because its miscibility with most organic solvents. The effectiveness of the Glu-TOH-Ti catalyst was also tested in water under the conditions of 0.2 mmol fructose, 20 mg catalyst, 4 mL water and at 140° C. for 30 min. The yield of HMF was only 8 mol % (entry 1 in Table 8), which may be due to rapid rehydration of HMF to the side products, levulinic and formic acids.[7] Thus, additional experiments were performed in water-MeTHF biphasic solvent in which HMF could accumulate in the MeTHF phase after its formation in the aqueous phase and hence can drive the dehydration reaction. MeTHF was chosen as an organic phase because it is green, cost-effective biorenewable alternative to oil-derived solvents, stable and has better extracting ability for furfurals.

The beneficial effect of water-MeTHF biphasic solvent was immediately realized when a reaction between 0.27 mmol fructose and 20 mg Glu-TsOH-Ti catalyst was carried out in the biphasic solvent system containing 4 mL MeTHF and 2 mL water at 140° C. As shown in entry 2 of Table 8, the reaction produced 26% HMF yield in 40 min. Upon increasing the reaction time from 40 min to 1 h, the yield of HMF improved from 26% to 34% (entry 3, Table 8). At higher temperature (180° C.), fructose dehydration under comparable reaction conditions produced 52% HMF in 10 min, followed by a slight increase in yield to 59% upon continuing the reaction to 60 min (entries 4-7, Table 8). Noteworthy, the conversions of fructose were about 30-40% higher than the observed HMF yields, suggesting a significant loss of either HMF or fructose under these reaction conditions.

TABLE 8

The catalytic effectiveness of Glu-TsOH-Ti for dehydration of Fructose,
Glucose, Cellbiose in water-MeTHF biphasic solvent.

| Entry # | Substrates (mmol) | Glu-TSOH-Ti (mg) | Solvent (mL) | T (° C.) | Time (min) | Conv. (%) | HMF Yield (mol %) UV | HMF Yield (mol %) HPLC |
|---|---|---|---|---|---|---|---|---|
| 1 | Fructose (0.27) | 20 | Water (4) | 140 | 30 | 18 | 8 | 6 |
| 2 | Fructose (0.27) | 20 | MeTHF (4)/$H_2O$ (2) | 140 | 40 | 20 | 26 | 23 |
| 3 | Fructose (0.27) | 20 | MeTHF (4)/$H_2O$ (2) | 140 | 60 | — | 34 | — |
| 4 | Fructose (0.2) | 22 | MeTHF (2)/$H_2O$ (1) | 180 | 10 | 81 | 52 | 46 |
| 5 | Fructose (0.2) | 22 | MeTHF (2)/$H_2O$ (1) | 180 | 20 | 87 | 56 | 51 |
| 6 | Fructose (0.2) | 22 | MeTHF (2)/$H_2O$ (1) | 180 | 30 | 93 | 56 | 51 |
| 7 | Fructose (0.2) | 22 | MeTHF (2)/$H_2O$ (1) | 180 | 60 | 99 | 59 | 55 |
| 8 | Glucose (0.28) | 23 | MeTHF (4)/$H_2O$ (2) | 180 | 10 | — | 18 | — |
| 9 | Glucose (0.28) | 23 | MeTHF (4)/$H_2O$ (2) | 180 | 60 | 61 | 31 | 30 |
| 10 | Glucose (0.28) | 23 | MeTHF (4)/$H_2O$ (2) | 180 | 120 | 73 | 46 | 43 |
| 11 | Glucose (0.28) | 22 | MeTHF (2)/$H_2O$ (1) | 220 | 120 | 90 | 48 | 48 |
| 12 | Cellobiose (0.2) | 23 | MeTHF (2)/$H_2O$ (1) | 180 | 10 | 94 | 26 | 22 |
| 13 | Cellobiose (0.2) | 23 | MeTHF (2)/$H_2O$ (1) | 180 | 20 | 94 | 36 | 32 |
| 14 | Cellobiose (0.2) | 23 | MeTHF (2)/$H_2O$ (1) | 180 | 60 | 100 | 39 | 35 |
| 15 | Sucrose (0.2) | 20 | MeTHF (2)/$H_2O$ (1) | 180 | 10 | — | — | 26 |
| 16 | Sucrose (0.2) | 20 | MeTHF (2) $H_2O$ (1) | 180 | 30 | — | — | 38 |

Figure 13:
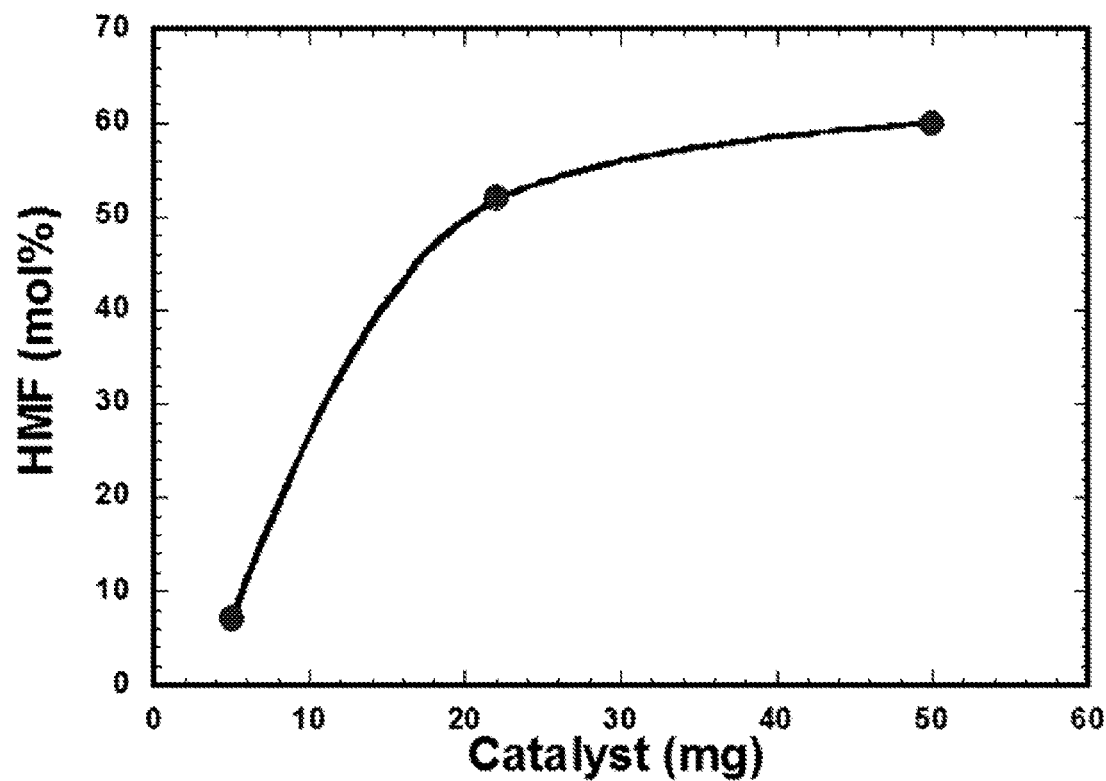
FIG. 13 shows the HMF yield as a function of Glu-TsOH-Ti catalyst dosages, under the following reaction conditions: fructose=0.2 mmol, T=180° C., and time=10 min.

To investigate the loss of the desired product, HMF, in the form of its rehydration products, levulinic and formic acids, $^1$H NMR spectrum of isolated HMF, obtained from reaction 6 (entry 6, Table 8), was recorded in acetone-$d_6$. This NMR spectrum showed the signals for formic acid and levulinic acid at δ8.2 and 2.2 ppm, respectively. The integrated signal intensity for formic acid-H was about 10% with respect to aldehyde-H intensity of HMF. Furthermore, the decomposition of HMF was separately studied for an aqueous solution of 0.2 mmol pure HMF at 140 and 180° C. in the presence of 24 mg catalyst. While degradation of HMF at 140° C. was not evidenced from a plot of HMF (%) versus time (deposited in supporting information), 8% decomposition of HMF was noted at 180° C. in 20 min. A significant loss of HMF, amounting to about 40%, was also reported at 180° C. for 1.5 hr in the case of Glu-TsOH catalyzed dehydration of fructose in DMSO. The effect of catalyst loading on the yield of HMF was also studied under the same reaction conditions listed in entry 4 of Table 8. Referring to FIG. 13 (which depicts the yield of HMF as a function of Glu-TsOH-Ti catalyst dosages for reaction conditions: Fructose=0.2 mmol; Catalyst=22 mg; T=180° C.; and time=10 minutes), the yield of HMF increased from 7% to 52% upon increasing the catalyst loading from 5 mg to 22 mg. A further increase in catalyst loading to 50 mg showed a small increase in yield to 60%. The heterogeneity of the catalyst was also tested by the hot-filtration experiment. In this experiment, 0.2 mmol fructose and 23 mg catalyst were reacted in water-MeTHF biphasic solvent at 140° C. for 2 min under microwave assisted heating. The temperature of the microwave reactor was needed to cool down to 70° C. to allow the reactor chamber open. The reaction mixture, after separating the solid catalyst through a 0.22 μm cut off syringe filter (25 mm diameter), was immediately transferred in a new microwave tube and the reaction was resumed without catalyst at 140° C. for another 18 min. UV-Vis spectrophotometric analysis of aliquots, collected at 2 and 20 min, showed similar HMF yields; 4.1 and 4.5 mol % in 2 and 20 min, respectively. This result confirms that the catalyst is indeed heterogeneous.

Although fructose has been the preferred feedstock for HMF production, its occurrence in nature is limited. This drives the attention to utilize more abundant carbohydrate, glucose, as raw material for HMF synthesis. As shown above, Glu-TsOH-Ti catalyst was effective for glucose dehydration in DMSO (vide supra); the major concern was (i) the appearance of black coloration in the solution primarily due to humin formation and (ii) the separation of HMF from DMSO solvent. Therefore, dehydration of glucose with the Glu-TsOH-Ti catalyst was carried out in water-MeTHF solvent at 180° C. The results as shown in Table 8 (entry 8) reveal the formation of 18% HMF in 10 min, which increased to 46% upon increasing the reaction time to 2 hr (entries 9 and 10, Table 8). To check the effect of temperature on glucose dehydration in water-MeTHF solvent, a reaction between 0.28 mmol glucose and 22 mg catalyst was carried out at 220° C. for 2 h, which produced 48% HMF (entry 11, Table 8); a little improvement in yield was observed at 180° C. It is also possible that the yield of HMF at higher temperature (220° C.) is undermined by its decomposition.

The scope of the present investigation was further extended for dehydration of cellobiose (a dimer of glucose units) and sucrose (a dimer of fructose and glucose units) with the Glu-TsOH-Ti catalyst. In case of cellobiose, the reaction steps are believed to involve (i) hydrolysis of cellobiose to glucose, (ii) isomerization of glucose to fructose followed by (iii) dehydration of fructose. A reaction between 0.22 mmol cellobiose and 23 mg catalyst in MeTHF-water biphasic solvent produced 26% HMF (entry 12, Table 8) in 10 min at 180° C. The yield of HMF increased from 22% to 32% upon continuing the reaction from 10 to 20 min followed by almost a plateau up to 60 min (entries 12-14, Table 8). Although the conversion of cellobiose was nearly 100%, HPLC analysis of the aqueous phase of the reaction solution showed the presence of a large amount of unconverted glucose and small amount of fructose (deposited in the supporting information). Previous reports on cellobiose dehydration with homogeneous $GeCl_4$ and $CrCl_3$ catalysts have shown the formation of 41% and 50% HMF, respectively, in pure or mixed [BMIM]Cl (BMIM=1-butyl-3methylimidazolium) ionic liquid. Compared to these reported HMF yields using toxic and non-separable Lewis acidic salts in ionic liquid, the present catalysis using bionenewable, non-toxic and recyclable Glu-TsOH-Ti catalyst in aqueous medium enabling 35% HMF is impressive and advances Green Chemistry applications. Under comparable reaction conditions, sucrose dehydration with Glu-TsOH-Ti catalyst produced a maximum of 38% HMF in 30 min at 180° C. (entries 15-16, Table 8). Higher yield of HMF from sucrose, a disaccharide of glucose and fructose units, can be explained by the fact that sucrose hydrolyzes to fructose and glucose units, both of which dehydrate to HMF.

Catalysis for Ff Production:

Ff, another platform chemical with an annual production of more than 200,000 tons, is a feedstock for 2-methylfuran, 2-MeTHF, furfural alcohol, ethyl levulinate and biofuels. While xylose dehydration usually proceeds via isomerization of xylose to xylulose followed by dehydration of xylulose to Ff, a direct route for xylose to Ff conversion has also been proposed in $AlCl_3$ catalyzed reaction. Dehydration of xylose in pure water is reported to suffer from poor Ff yield because of hydration and oligomerization of Ff to unwanted side products. In this context, higher Ff yield (56%) in DMA-LiCl solvent has been reported by Binder el at. using a catalytic system comprising a Lewis acidic Cr(II) or Cr(III) halide and Brønsted acid HCl. Recent studies on conversion of xylose, xylane, lignocellulosic biomass (corn stover, pinewood, switchgrass and poplar) with homogeneous catalysts, such as maleic acid, $AlCl_3$, $FeCl_3$, reported higher Ff yields in biphasic solvent systems (water-THF or water-MeTHF). Because of potential benefit of heterogeneous catalyst over homogeneous, here we investigated the catalytic effectiveness of sulfonated carbonaceous material, containing Brønsted and Lewis acidic sites, for Ff production from xylose.

Figure 14:
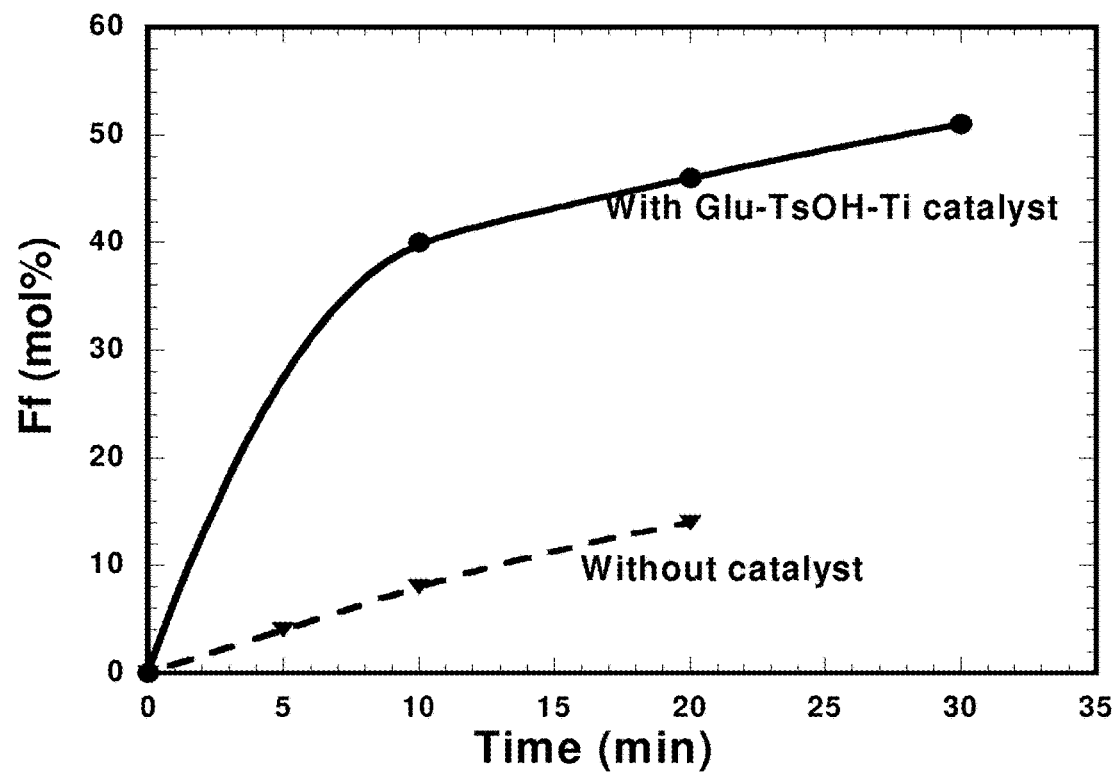
FIG. 14 shows the yield of Ff from xylose with and without the Glu-TsOH-Ti catalyst, under the following reaction conditions: 0.33 mmol xylose, 22 mg Glu-TsOH-Ti, 180° C., 2 mL MeTHF and 1 mL water.

Preliminary experiments for the conversion of xylose to Ff were carried out in DMSO and DMA (N,N-dimethylacetamide)-LiCl (10 wt % LiCl) solvents. A reaction between 0.7 mmol xylose and 50 mg Glu-TsOH-Ti catalyst at 140° C. produced 51% Ff in 60 min. In case of DMA-LiCl solvent mediated reaction between 0.33 mmol xylose and 20 mg catalyst at 180° C., a maximum 37% Ff was recorded in 5 min. The yield remained almost constant upon further increasing the reaction time to 60 min. A previous report has shown the formation of 56% Ff in 4 hr in DMA-LiCl solvent from HCl/Cr(II)-Cr(III) catalyzed dehydration of xylose at 100° C.[37] In comparison to 56% yield using mineral acid/Cr(II)-Cr(III) catalyst, the observed 51% Ff yield in the present reaction using heterogeneous catalyst is significant. However, to avoid the complexity of Ff extraction and purification from these organic solvents, the subsequent experiments for the conversion of xylose to Ff were carried out in water-MeTHF biphasic solvent. The yields of Ff from a reaction between 0.33 mmol xylose and 22 mg Glu-TsOH-Ti catalyst at 180° C. in water-MeTHF solvent were monitored as a function of time. Referring to FIG. 14 (depicting the yield of Ff from xylose with and without Glu-TsOH-Ti catalyst, under reaction conditions: 0.33 mmol xylose, 22 mg Glu-TsOH-Ti, 180° C., 2 mL MeTHF and 1 mL water), the results as plotted revealed the formation of maximum 51% Ff during the experimental time of 30 min. In parallel, control experiments were also performed without the catalyst. A comparison of Ff yields with and without catalyst (FIG. 14) further confirms that the investigated heterogeneous catalyst, having Brønsted and Lewis acidic sites, is effective for xylose conversion in aqueous phase.

Similar to glucose dehydration, the conversion of xylose to Ff is known to occur via the formation of xylulose intermediate. This argument was supported by higher Ff yield from xylulose as a starting substrate than that from xylose under comparable reaction conditions. However, a direct route for xylose to Ff has recently been proposed in $AlCl_3$ catalyzed dehydration of xylose. To further investigate the pathway of xylose dehydration with the Glu-TsOH-Ti catalyst, we studied a reaction between 0.3 mmol xylulose and 21 mg catalyst in water-MeTHF at 180° C. Surprisingly, the reaction produced only 6 mol % Ff in 10 min, which is significantly lower than that obtained from xylose (FIG. 14). The yield did not increase upon increasing the reaction time to 30 min. This result suggests that xylose dehydration with the Glu-TsOH-Ti catalyst follows a different pathway other than the xylulose intermediate, and requires a separate study to explore the mechanism in detail.

Figure 15:
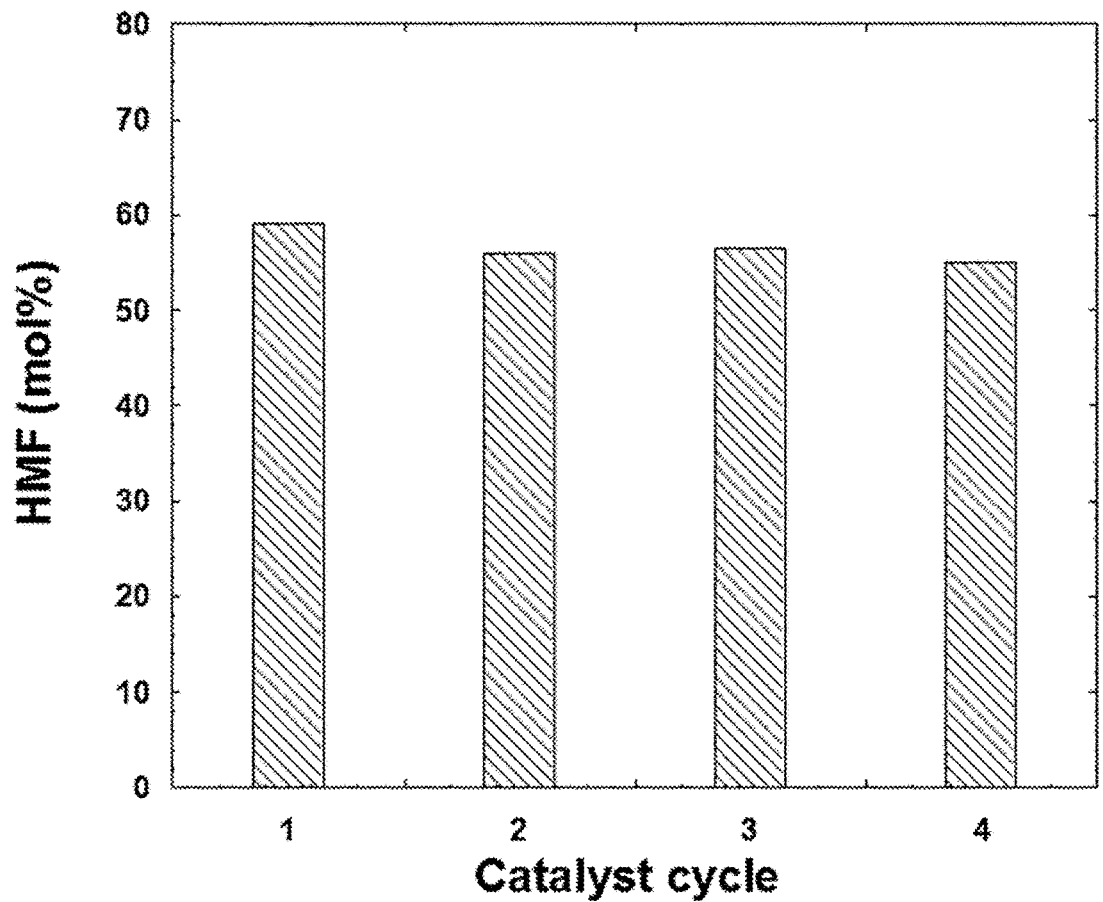
FIG. 15 shows the results of the recyclability study of the Glu-TsOH-Ti catalyst for dehydration of fructose to HMF in water-MeTHF biphasic solvent at 180° C. for 60 minutes.

Catalyst Recyclability:

The reusability of the Glu-TsOH-Ti catalyst was examined for fructose dehydration in water-MeTHF solvent by carrying out a reaction between 0.2 mmol fructose and 22 mg catalyst at 180° C. for 60 min. After completion of reaction for 60 min, an aliquot was collected for analysis, and the solid catalyst left in the tube was collected and reused for three more cycles by adding fresh substrate and solvent. Fresh catalyst was not added to compensate for any loss of catalyst during recovery. The organic and aqueous phases of the reaction solution of each run were analyzed separately to quantify the total amount of HMF formation. As shown in FIG. 15 (depicting the results of the recyclability study of the Glu-TsOH-Ti catalyst for dehydration of fructose to HMF in water-MeTHF biphasic solvent at 180° C. for 60 min.), the loss of activity of the catalyst, in terms of HMF yield, after four cycles was negligible.

Thus, the present Ti-containing carbonaceous material based on cheap and biorenewable carbon support represents a sustainable catalyst for the production of furfurals, platform chemicals for biofuels and valuable chemicals, in an environmentally benign solvent.

Self-assembled nanopaticulate of sulfonated carbonaceous material having Brønsted sulfonic acid group and Lewis acidic titania pores has been synthesized through thermal treatment of biorenewarble glucose, p-toluene sulfonic acid and titanium isopropoxide. The presence of sulfonic acid group and Lewis acidity in the material has been confirmed by FT-IR and Py-FT-IR methods. This material shows good catalytic activity for the dehydration of biomass derived fructose, glucose, cellobiose and sucrose to HMF, a platform chemical for biofuel and valuable chemicals, and also catalyzes the conversion of xylose to Ff. Under microwave assisted heating, fructose, glucose cellobiose and sucrose dehydration reaction with the Glu-TsOH-Ti catalyst enables maximum yields of 59, 48, 35 and 38% of HMF, respectively, in water-MeTHF biphasic solvent system. Higher yield of HMF (99%) is observed in DMSO for the dehydration of fructose. In case of xylose, a maximum yield of 51% of Ff has been recorded in the same biphasic solvent. Experiments employing xylulose as a starting substrate yielded significantly less Ff and as a result the involvement of xylulose as an intermediate in xylose dehydration has been ruled out. The recyclability experiments show that the catalyst retained full activity after four consecutive cycles; a loss in activity, in terms of HMF yield, was only 3%.

Additional disclosure is found in Appendix-A, filed herewith, entirety of which is incorporated herein by reference into the present disclosure.

While the disclosures have been illustrated and described in detail in the drawings and foregoing description, the same is to be considered as illustrative and not restrictive in character, it being understood that only certain embodiments have been shown and described and that all changes and modifications that come within the spirit of the disclosure are desired to be protected.

REFERENCES

1. T. D. Matson, K. Barta, A. V. Iretskii, P. C. Ford, *J. Am. Chem. Soc.*, 133, 14090 (2011).
2. J. Ragauskas, C. K. Williams, B. H. Davidson, G. Britovsek, J. Cairney, W. J. Frederick, J. P. Hallett, D. J. Leak, C. L. Liotta, J. R. Mielenz, R. Murphy, R. Templet and T. Tschaplinski, *Science*, 2006, 311, 484 and references therein.
3. T. Werpy, G. Petersen in Top Value Added Chemicals from Biomass, Volume I, Results of
Screening for Potential Candidates from Sugar and Synthesis Gas, US Department of Energy DOE/GO-102004-1992, August 2004. www.eere.energy.gov/biomass/pdfs/35523.pdf.
4. (a) G. W. Huber, J. N. Chheda, C. J. Barrett and J. A. Dumesic, *Prodcution of Liquid Alkanes by Aqueous-Phase Processing of Biomass-Derived Carbohydrates*, Science, 2005, 308(5727), 1446-1450; (b) A. Boisen, T. Christensen, W. Fu, Y. Gorbanev, T. Hansen, J. Jensen, S. Klitgaard, S. Pedersen, A. Riisager, T. St°ahlberg and J. Woodley, *Chem. Eng. Res. Des.*, 2009, 87, 1318.
5. S. Dutta, S. De, B. Saha and I. Alam, *Catal. Sci. Tech.*, 2012, DOI: 10.1039/c2cy20235b and references therein.
6. J. B. Binder and R. T. Raines, *J. Am. Chem. Soc.*, 2009, 131, 1979.
7. H. Zhao, J. E. Holladay, H. Brown and Z. C. Zhang, *Science*, 2007, 316, 1597.
8. S. De, S. Dutta and B. Saha, *Green Chem.* 2011, 13, 2859 and references therein.
9. Y. yang, C. Hu and M. M. Abu-Omar, *Green Chem.* 2012, 14. 509.
10. S. Hu, Z. Zhang, J. Song, Y. Zhou and B. Han, *Green Chem.*, 2009, 11, 1746.
11. J. Y. Gerentt and Y. Zhang, *ChemSusChem*, 2009, 2, 731.
12. E. S. Kim, S. Liu, M. M. Abu-Omar and N. S. Mosier, *Energy & Fuels*, 2012, DOI: 10.1021/ef2014106.
13. S. Dutta, S. De, I. Alam and M. M. Abu-Omar, *J. Catal.*, 2012, 288, 8.
14. S. Zhao, M. Cheng, J. Li, J. Tian and X. Wang, *Chem. Commun.*, 2011, 47, 2176.
15. I. Alam, S. De, S. Dutta and B. Saha, RSC Adv. 2012, DOI: 10.1039/c2ra20574b
16. X. Qi, M. Watanabe, T. M. Aida and R. L. Smith, Jr., *Catal. Commun.*, 2008, 9, 2244.
17. M. Watanabe, Y. Aizawa, T. Lida, R. Nishimura and H. Inomata, *Appl. Catal., A*, 2005, 295, 150.
18. (a) S. De, S. Dutta, A. K. Patra, A. Bhaumik and B. Saha, *J. Mater. Chem*, 2011, 21, 17505. (b) A. Dutta, A. K. Patra, S. Dutta, B. Saha and A. Bhaumik, *J. Mater. Chem.* 2012, 22, 14094. (c) S. Dutta, S. De, A. K. Patra, M. Sasidharan, A. Bhaumik and B. Saha, *Appl. Catal. A: Gen.* 2011, 409-410, 133. (d) S. De, S. Dutta, A. K. Patra, B. S. Rana, A. K. Sinha, B. Saha and A. Bhaumik, 2012, *Appl. Catal. A: Gen.* 2012, 435-436, 197.
19. B. Kasprzyk-Hordern, *Adv. Colloid Interface Sci.*, 2004, 110, 19.
20. T. Okuhara, *Chem. Rev.*, 2002, 102, 3641.
21. E. Lam, J. H. Chong, E. Majid, Y. Liu, S. Hrapovic, A. C. W. Leung and J. H. T. Luong, *Carbon*, 2012, 50, 1033.
22. M. Toda, A. Takagaki, M. Okamura, J. N. Kondo, S. Hayashi, K. Domen, M. Hara, *Nature*, 2005, 438, 178.
23. R. Xing, Y. Liu, Y. Wang, L. Chen, H. Wu, Y. Jiang, M. He and P. Wu, *Microporous Mesoporous Mater.*, 2007, 105, 41.
24. V. L. Budarin, J. H. Clark, R. Luque, D. J. Macquarrie, *Chem. Commun.*, 2007, 634.
25. B. Zhang, J. Ren, Xiaohui Liu, Y. Guo, Y. Guo, G. Lu and Y. Wang, *Catal. Comm.*, 2010, 1, 629.
26. J. Wang, W. Xu, J. Ren, X. Liu, G. Lu and Y. Wang, *Green Chem.*, 2011, 13, 2678.
27. R. Weingarten. G. A. Tompsett, W. C. Conner Jr. and G. W. Huber, *J. Catal.*, 2011, 279, 174.
28. (a) A. K. Patra, S. K. Das and A. Bhaumik, *J. Mater. Chem.*, 2011, 21, 3925, (b) S. Dutta, A. K. Patra, S. De, A. Bhaumik, and B. Saha, *ACS Appl. Mater. Interfaces*, 2012, 4, 1560.
29. S. K. Das, M. K. Bhunia, A. K. Sinha and A. Bhaumik, *ACS Catal.*, 2011, 1, 493, 57.
30. R. W. Stevens, S. S. C. Chuang and B. H. Davis, *Appl. Catal. A: Gen.*, 2003, 252, 57.
31. S. K. Das, M. K. Bhunia, A. K. Sinha and A. Bhaumik, *J. Phys. Chem. C*, 2009, 113, 8918.
32. S. Lowell, J. E. Shields, M. A. Thomas and M. Thommes, Characterization of Porous Solids and Powders: Surface Area, Pore Size, and Density Springer, 2010.
33. S. J. Dee and A. T. Bell, *ChemSusChem*, 2012, 4, 1166.
34. Y. J. Pag'an-Torres, T. Wang, J. M. R. Gallo, B. H. Shanks and J. A. Dumesic, *ACS catalysis*, 2012, 2, 930.
35. (a) Z. Zhang, Q. Wang, H. Xe, W. Liu and Z. K. Zhao, *ChemSusChem*, 2011, 4, 131. (b) S. Lima, P. Neves, M. M. Antunes, M. Pillinger, N. Ignatyev and A. A. Valente, *Appl. Catal. A: Gen.*, 2009, 363, 93.
36. Y. Yang, C.-W. Hu and M.-M. Abu-Omar, *ChemSusChem*, 2012, 5, 405.
37. M. J. Climent, A. Corma and S. Iborra, *Green Chem.*, 2011, 13, 520.
38. J. B. Binder, J. J. Blank, A. V. Cefali and R. T. Raines, *ChemSusChefin*, 2010, 3, 1268.
39. T. Vom Stein, P. M. Grande, W. Leitner and P. D. De Maria, *ChemSusChem*, 2011, 4, 1592.
40. V. Choudhary, A. B. Pinat, S. I. Sandler, D. G. Vlachos and R. F. Lobo, *ACS Catal.*, 2011, 1, 1724.
41. Rakesh, A. and R. S. Navneet, *Synergistic routes to liquid fuel for a petroleum-deprived future*, 2009, p. 1898-1905.
42. Huber, G. W. and J. A. Dumesic, *An overview of aqueous-phase catalytic processes for production of hydrogen and alkanes in a biorefinery*, Catalysis Today, 2006, 111(1-2): p. 119-132.
43. Davda, R. R., et al., *A review of catalytic issues and process conditions for renewable hydrogen and alkanes by aqueous-phase reforming of oxygenated hydrocarbons over supported metal catalysts*, Applied Catalysis B: Enfironmental, 2005, 56(1-2): p. 171-186.
44. Cortright, R. D., R. R. Davda, and J. A. Dumesic, *Hydrogen from catalytic reforming of biomass-derived hydrocarbons in liquid water*, Nature, 2002, 418: p. 964-967.
45. Serrano-Ruiz, J. C., R. M. West, and J. A. Dumesic, *Catalytic Conversion of Renewable Biomass Resources to Fuels and Chemicals*, Annual Review of Chemical and Biomolecular Engineering, 2010, 1(1): p. 79-100.
46. Roberts, V. M., et al., *Towards Quantitative Catalytic Lignin Depolymerization*, Chemistry—A European Journal, 17(21): p. 5939-5948.
47. Zhao, C., et al., *Aqueous-phase hydrodeoxygenation of bio-derived phenols to cycloalkanes*, Journal of Catalysis, 280(1): p. 8-16.

48. Zhao, C., D. M. Camaioni, and J. A. Lercher, *Selective catalytic hydroalkylation and deoxygenation of substituted phenols to biclycloalkanes*, Journal of Catalysis, 288(0): p. 92-103.
49. Zhao, C. and J. A. Lercher, *Selective Hydrodeoxygenation of Lignin-Derived phenolic Monomers and Dimers to Cycloalkanes on Pd/C and HZSM-5 catalysts*, ChemCatChem., 4(1): p. 64-68.
50. Kunkes, E. L., E. I. Gurbuz, and J. A. Dumesic, *Vapour-phase C-C coupling reactions of biomass-derived oxygenates over Pd/CeZrOx catalysts*, Journal of Catalysis, 2009, 266(2): p. 236-239.
51. Zhu, X., R. G. Mallinson, and D. E. Resasco, *Role of transalkylation reactions in the conversion of anisole over HZSM-5*, Applied Catalysis A: General, 2010, In Press, Corrected Proof.
52. Gonzalez-Borja, M. A. and D. E. Resasco, *An and Guaiacol Hydrodeoxygenation over Monolithic Pt—Sn Catalysts*, Energy & Fuels, 2011.
53. Sitthisa, S. and D. Resasco, *Hydrodeoxygenation of Furfural over Supported Metal Catalysts: a comparative study of Cu, Pd, and Ni*, Catalysis Letters, 141(6): p. 784-791.
54. Sun, J., et al., *Carbon-supported bimetallic Pd—Fe catalysts for vapor-phase hydrodeoxygenation of guaiacol*, Journal of Catalysis, 306(0): p. 47-57.
55. Rakesh Agrawal, Manju Agrawal, and Navneet R. Singh, *Novel process for producing liquid hydrocarbon by pyrolysis of biomass in presence of hydrogen from a carbon-free energy source*, U.S. Patent Application No. 60/968,194 (2007).
56. Antos, G. J. and A. M. Aitani, *Catalytic naptha reforming*, Vol. 100, 2004: CRC Press.
57. Lopez, L. L.; Tiller, P. R.; Senko, M. W.; Schwartz, J. C. *Rapid Commun. Mass Spectrom.* 13, 663-668 (1999).
58. T. H. Parsell, B. C. Owen, I. Klein, T. M. Jarrell, C. L. Marcum, L. J. Haupert, L. M. Amundson, H. I. Kenttamaa, F. Ribeiro, J. T. Miller, M. M. Abu-Omar, *Chem. Sci.* 4, 806 (2013).
59. Haupert, L. J.; Owen, B. C.; Marcum, C. L.; Jarrell, T. M.; Pulliam, C. J.; Amundson, L. M.; Narra, P.; Aqueel, M. S.; Parsell, T. H.; Abu-Omar, M. M.; Kenttamaa, H. I. *Fuel* 95, 634-641 (2012).
60. A. Sluiter, B. Hames, R. Ruiz, C. Scarlata, J. Suiter, D. Templeton, D. Crocker, *Determination of Structural Carbohydrates and Lignin in Biomass*. NREL/TP-510-42618.
61. J. Ralph, T. Akiyama, H. Kim, F. Lu, P. F. Schatz, J. M. Marita, S. A. Ralph, M. S. S. Reddy, F. Chen, R. A, Dixon, *J. Biol. Chem.* 281, 8843-8853 (2006).
62. R. S. Fukushima, R. D. Hatfield, *J. Agric. Food Chem.* 49, 3133-3139 (2001).
63. A. Sluiter, B. Hames, R. Ruiz, C. Scarlata, J. Sluiter, D. Templeton, *Determination of Sugars, Byproducts, and Degradation Products in Liquid Fraction Process Samples*. NREL/TP-510-42623 (2008).
64. Jing-Ke Weng, T. Akiyama, N. D. Bonawitz, X. Li, J. Ralph, C. Chapple, *Plant Cell.* 22, 1620-1623 (2010).
65. A. Sluiter, R. Ruiz, C. Scarlata, J. Suiter, and D. Templeton, *Determination of Extractives in Biomass (LAP)*. NREL/TP-510-42619.
66. C. E. Wyman, B. E. Dale, R. T. Elander, M. Holtzapple, M. R. Ladisch, Y. Y. Lee, C. Mitchinson, J. N. Saddler, *Biotechnol. Prog.* 25, 333-339 (2009).
67. Q. Song, F. Wang, J. Cai, Y. Wang, J. Zhang, W. Yu, J. Xu, *Energy Environ. Sci.* 6, 994 (2013).
68. Chinese dihydroeugenol Industrial Research Report, *China Market Research Center (CMRC)*, 2009-2010.
69. T. D. Matson, K. Barta, A. V. Iretskii, P. C. Ford, *J. Am. Chem. Soc.* 133, 14090 (2011).
70. Q. Song, F. Wang, J. Xu, *Green Chem.* 48, 7019 (2012).
71. A. C. Atesin, N. A. Ray, P. C. Stair, T. J. Marks, *J. Am. Chem. Soc.* 134, 14682-14685 (2012).
72. R. N. Olcese, G. Lardier, M. Bettahar, J. Ghanbaja, S. Fontana, V. Carré, F. Aubriet, D. Petitjean, A. Dufour, *ChemSusChem* 6, ASAP (DOI: 10.1001/cssc.201300191) (2013).
73. W. Xu, S. J. Miller, P. K. Agrawal, C. W. Jones, *ChemSusChem* 5, 667 (2012).
74. N. Joshi, A. Lawal, *Ind. Eng. Chem. Res.* 52, 4049 (2013). (d) A. L. Jongerius, R. Jastrzebski, P. C. A. Brujnincx, B. M. Weckhuysen, *J. Cat.* 285, 315 (2012).
75. Z. Strassberger, A. H. Alberts, M. J. Louwerse, S. Tanase, G. Rothenberg, *Green Chem.* 15, 768 (2013).
76. A. G. Sergeev, J. F. Hartwig, *Science* 332, 439 (2011).
77. J. Van Haveren, E. L. Scott, J. Sanders, *Biofuels Bioprod. Bioref.* 2, 41 (2008).
78. H. R. Bjørsvik, F. Minisci, *Org. Process Res. Dev.* 3, 330 (1999).
79. J. Zakzeski, P. C. A. Bruijnincx, A. L. Jongerius, B. M. Weckhuysen, *Chem. Rev.* 110, 3552 (2010).
80. A. J. Crisci, M. H. Tuckers, M.-Y. Lee, S. G. Lang, J. A. Dumesic, S. L. Scott, *ACS Catal.* 1, 719 (2011).
81. S. K. Hanson, R. T. Baker, J. C. Gordon, B. L. Scott, A. D. Sutton, D. L. Thorn, *J. Am. Chem. Soc.* 130, 428 (2009).
82. G. W. Huber, J. W. Shabaker, J. A. Dumesic, *Science* 300, 2075 (2003).
83. R. F. Service, *Science* 339, 1374 (2013).
84. CEN-Online, *Production: Growth in Most Regions*, 67-76, Jul. 11, 2005, http://pubs.acs.org/cen/coverstory/83/pdf/8328production.pdf.

The invention claimed is:
1. A delignification process comprising treating biomass with a selective hydrodeoxygenation catalyst to form 2-methoxy-4-propylphenol, 2,6-dimethoxy-4-propylphenol, or mixtures thereof, wherein the hydrodeoxygenation catalyst comprises palladium and zinc.
2. The process of claim 1, wherein the process is performed in a single step.
3. The process of claim 1, wherein the hydrodeoxygenation catalyst comprises zinc and palladium on carbon.
4. The process of claim 3, wherein the palladium on carbon is a nanoparticulate.
5. The process of claim 3, wherein the biomass is wood biomass.
6. The process of claim 5, wherein a single product stream is created in the liquid phase comprising 2-methoxy-4-propylphenol, 2,6-dimethoxy-4-propylphenol, or mixtures thereof.
7. The process of claim 6, wherein the percentage by mass of 2-methoxy-4-propylphenol in the single product stream is between about 17% and about 100%.
8. The process of claim 1, wherein cellulose remaining in the biomass after processing is suitable for further processing into liquid fuels or other chemicals.
9. A process for preparing liquid transportation fuels comprising treating biomass with a selective hydrodeoxygenation catalyst to form 2-methoxy-4-propylphenol, 2,6-dimethoxy-4-propylphenol, or mixtures thereof to form a single product liquid stream, wherein the selective hydrodeoxygenation catalyst comprises palladium and zinc; and catalytically hydrogenating the liquid stream to prepare liquid transportation fuels.

10. The process of claim 9, wherein propylbenzene is a liquid transportation fuel.

11. The process of claim 10, wherein the catalyst for hydrogenation is PtMo.

12. The process of claim 9, wherein vapor-phase products from the treatment of a selective hydrodeoxygenation catalyst are catalytically dehydrogenated to form liquid transportation fuels.

13. The process of claim 11, wherein the PtMo catalyst is supported on multi-walled carbon nanotubes.

14. The process of claim 9, wherein the catalyst is a bimetallic catalyst wherein one metal is selected from the group consisting of Pt, Pd, Ni, Ru, Rh, Co, and Fe and the other metal is selected from the group consisting of Ti, V, Nb, Cr, Mo, W, Re, Fe, and Cu and wherein the catalyst is supported on a support selected from the group consisting of multi-walled carbon nanotubes, carbon, silicon dioxide, aluminum oxide, silica-aluminate, and a zeolite.

15. The process of claim 9, wherein the catalytically hydrogenating the liquid stream to prepare liquid transportation fuels is done in a suitable high-pressure reactor.

\* \* \* \* \*